United States Patent
Vuskovic et al.

(10) Patent No.: US 9,734,122 B2
(45) Date of Patent: Aug. 15, 2017

(54) SYSTEM, METHOD AND COMPUTER-ACCESSIBLE MEDIUM FOR EVALUATING A MALIGNANCY STATUS IN AT-RISK POPULATIONS AND DURING PATIENT TREATMENT MANAGEMENT

(75) Inventors: Marko I. Vuskovic, Bonsall, CA (US); Margaret E. Huflejt, La Jolla, CA (US); Harvey I. Pass, Bronxville, NY (US)

(73) Assignee: New York University, New York, NY (US)

( * ) Notice: Subject to any disclaimer, the term of this patent is extended or adjusted under 35 U.S.C. 154(b) by 1198 days.

(21) Appl. No.: 13/636,432

(22) PCT Filed: Mar. 25, 2011

(86) PCT No.: PCT/US2011/030005
§ 371 (c)(1),
(2), (4) Date: Dec. 6, 2012

(87) PCT Pub. No.: WO2011/119967
PCT Pub. Date: Sep. 29, 2011

(65) Prior Publication Data
US 2013/0080101 A1 Mar. 28, 2013

Related U.S. Application Data

(60) Provisional application No. 61/318,144, filed on Mar. 26, 2010.

(51) Int. Cl.
*G01N 33/48* (2006.01)
*G01N 33/50* (2006.01)
*G06F 15/00* (2006.01)
*G06F 19/24* (2011.01)
*G06F 19/26* (2011.01)
*G06F 17/30* (2006.01)

(52) U.S. Cl.
CPC ........ *G06F 15/00* (2013.01); *G06F 17/30595* (2013.01); *G06F 19/24* (2013.01); *G06F 19/26* (2013.01)

(58) Field of Classification Search
None
See application file for complete search history.

(56) References Cited

U.S. PATENT DOCUMENTS

| 6,656,115 | B1 | 12/2003 | Miyazaki et al. |
| 2003/0187615 | A1 | 10/2003 | Epler et al. |
| 2009/0276287 | A1 | 11/2009 | Firouzbakht et al. |

FOREIGN PATENT DOCUMENTS

| JP | 10-134084 | 5/1998 |
| WO | WO 2005/088310 A2 * | 9/2005 |

OTHER PUBLICATIONS

Golub et al. Molecular classification of cancer: class discovery and class prediction by gene expression monitoring. Science, vol. 286, 1999, pp. 531-537.*
International Search Report for PCT/US2011/030005 mailed Dec. 23, 2011.
International Written Opinion for PCT/US2011/030005 mailed Dec. 23, 2011.
Platt, J.C. "Probabilistic outputs for support vector machines & comparison to regularized likelihood methods", Adv. in. Lar. Mar. Classifiers, Cambridge, MA, MIT Press 1999.

* cited by examiner

*Primary Examiner* — Russell S Negin
(74) *Attorney, Agent, or Firm* — Andrews Kurth Kenyon LLP

(57) ABSTRACT

In accordance with certain exemplary embodiments of the present disclosure, exemplary visualization system, method, procedure and computer-accessible medium can be provided, which individually and/or collectively can be called, e.g., ImmunoRuler (IR). Certain exemplary embodiments of the exemplary IR in accordance with the present disclosure can be used for, e.g., comparing two groups of objects with specific and distinguished properties, such as a group of case subjects with a particular disease and a group of control subjects without that particular disease, and/or a group of subjects with a particular disease who are given a treatment and a group of subjects with the same disease but under another treatment or no treatment at all.

26 Claims, 13 Drawing Sheets

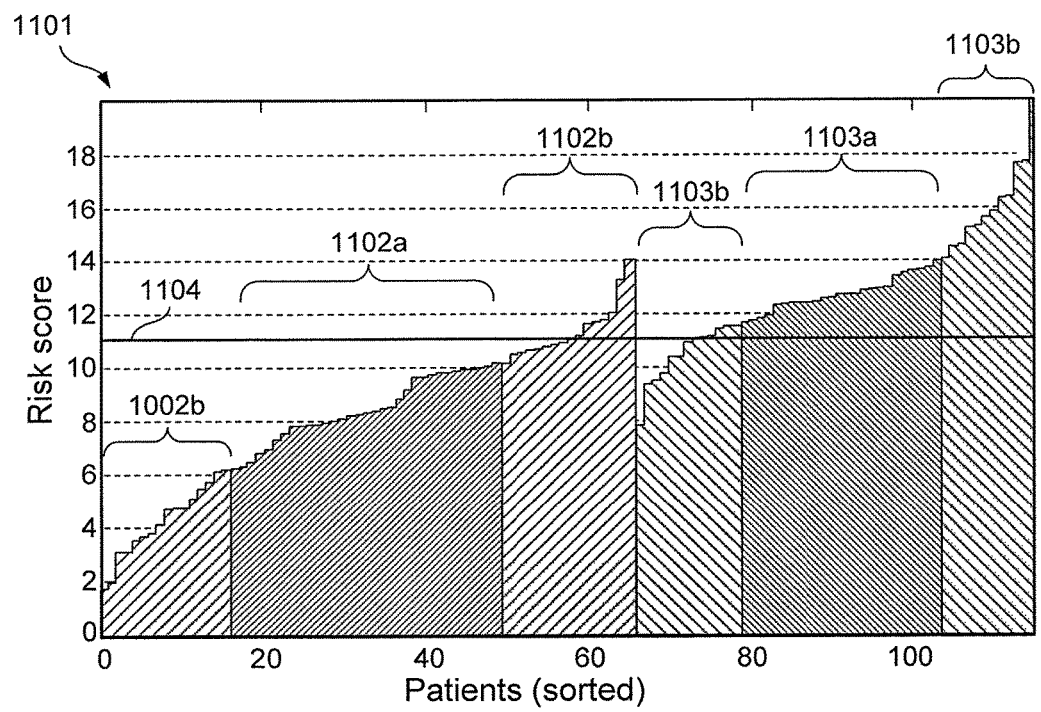
F I G. 11
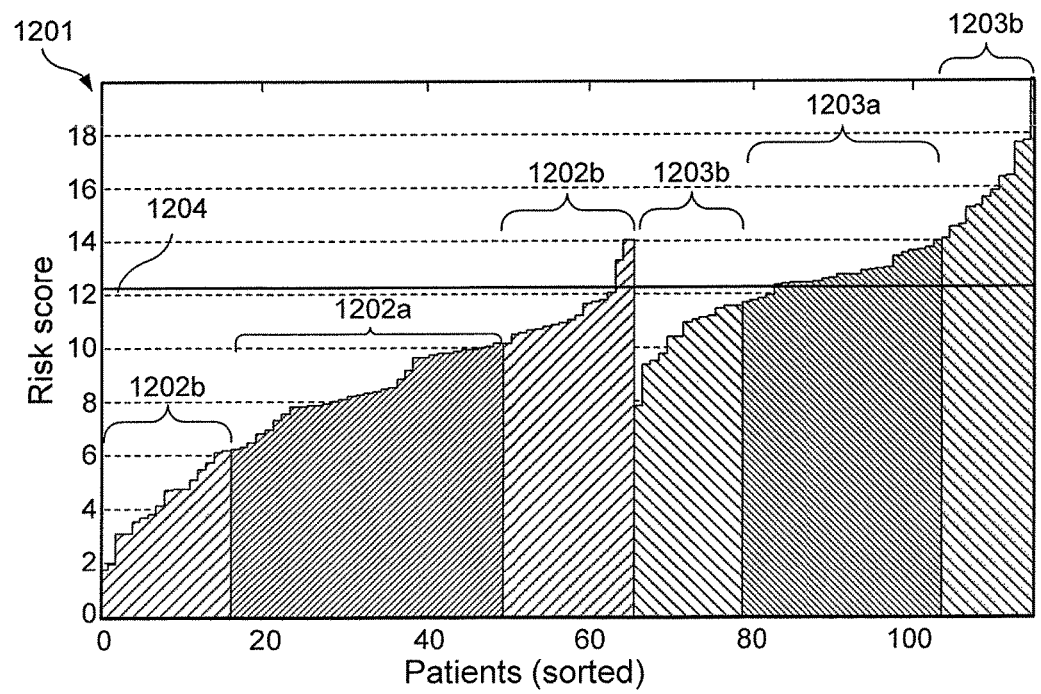
F I G. 12

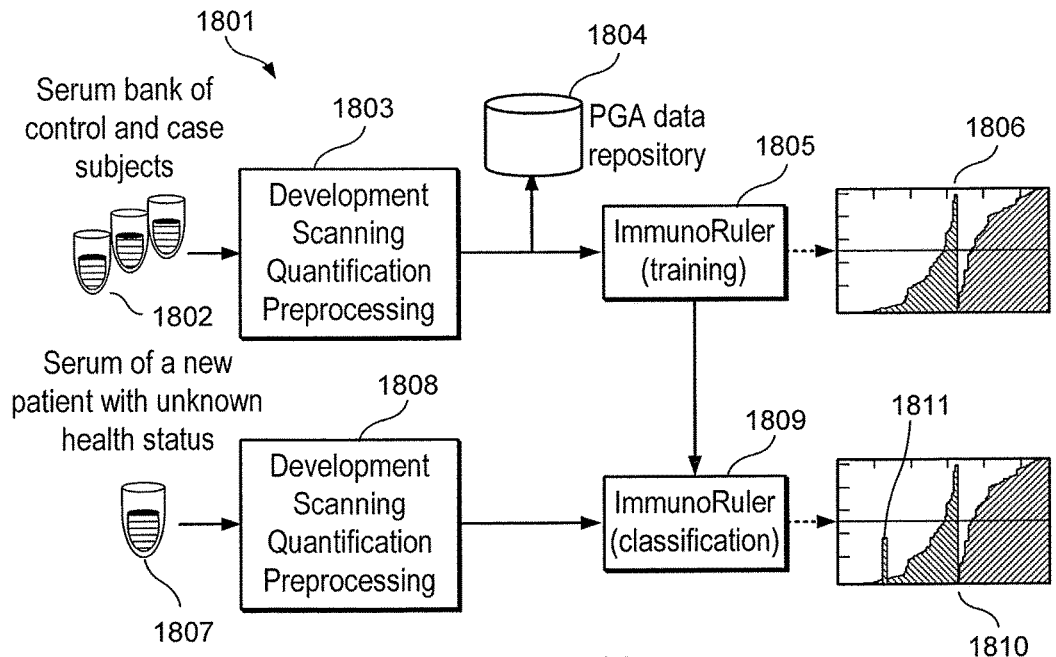
F I G. 18
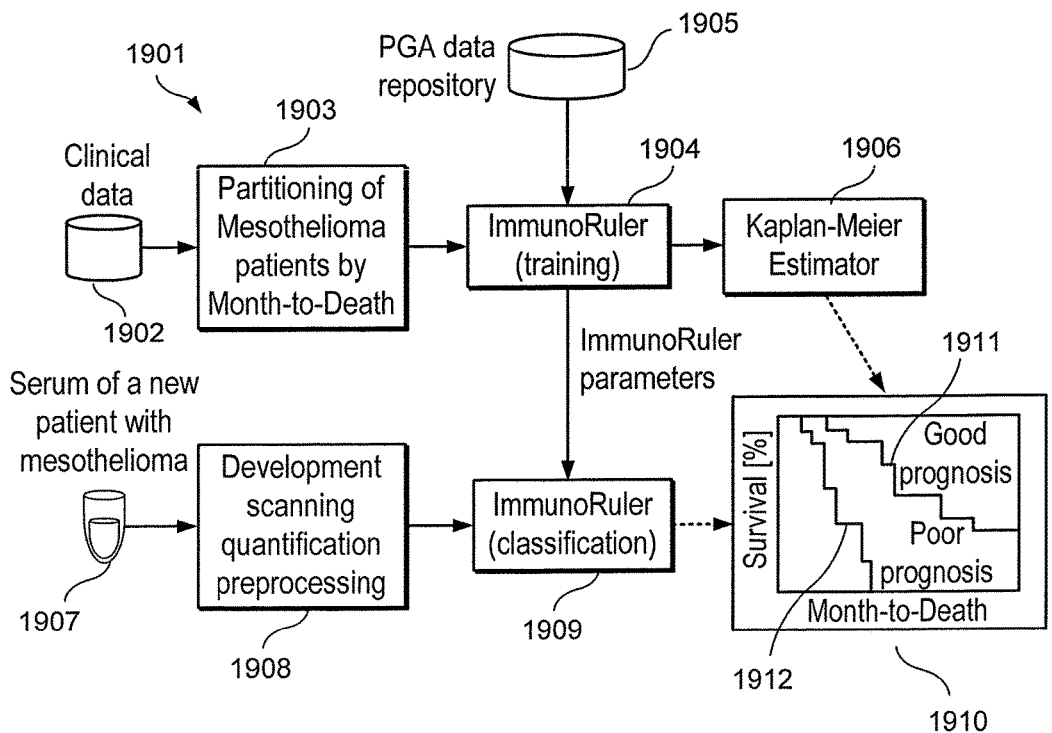
F I G. 19

SYSTEM, METHOD AND COMPUTER-ACCESSIBLE MEDIUM FOR EVALUATING A MALIGNANCY STATUS IN AT-RISK POPULATIONS AND DURING PATIENT TREATMENT MANAGEMENT

CROSS-REFERENCE TO RELATED APPLICATION(S)

The present application relates to and claims priority from International Patent Application No. PCT/US2011/030005 filed on Mar. 25, 2011, and from U.S. Provisional Application Ser. No. 61/318,144, filed Mar. 26, 2010, the entire disclosures of which are incorporated by reference herein in its entirety.

STATEMENT REGARDING FEDERALLY SPONSORED RESEARCH

The present disclosure was developed, at least in part, using Government support under NCI Grant No. 1U01CA128526 awarded by the National Cancer Institute. Therefore, the Federal Government may have certain rights in the invention.

FIELD OF THE DISCLOSURE

Exemplary embodiments of the present disclosure relate generally to exemplary systems, methods, and computer-accessible media for, e.g., obtaining information associated with at least one sample from a plurality of groups, and more particularly to determining further information based on the obtained information.

BACKGROUND INFORMATION

It can be beneficial to provide a cost effective test for early detection, diagnosis and prognosis of certain diseases, especially for cancers. Several approaches have been investigated including, e.g., proteomics and genomics based markers. For example, Printed Glycan Arrays (PGA), has been recently developed as a high-throughput platform that can provide a quantitative assessment of a systemic immuno response by measuring the levels of binding of antibodies present in serum to various carbohydrate structures (glycans) printed on a "glycochip". However, there can be certain deficiencies associated with PGA and related technologies, such as how associated information is obtained and stored for future use and/or applications (e.g., training a system based on historical information) and how the information can be presented to a user (e.g., to provide for improved, easier and/or quicker visualization and comparison). Thus, it can be beneficial to overcome such deficiencies.

Accordingly, there may be a need or a benefit to address and/or overcome at least some of the issues and/or deficiencies described herein above.

SUMMARY OF EXEMPLARY EMBODIMENTS OF THE DISCLOSURE

Certain exemplary embodiments in accordance with the present disclosure can use PGA for delivering antiglycan antibody-based biomarkers of various stages of malignant transformation. Exemplary computer-accessible medium, systems, and methods in accordance with the present disclosure can collectively and/or individually be called, e.g., "ImmunoRuler" (IR), which can be considered to be a bioinformatics system that can be used for, e.g., biomarker discovery and early detection, diagnosis, and prognosis of cancers, as well as patient treatment management. According to certain exemplary embodiments of the present disclosure, the exemplary IR can be used, for example, in a complementary manner with a PGA-generated, anti-glycan antibody-based immunoprofiles.

Certain exemplary embodiments of the present disclosure can address the exemplary problems and/or overcome the exemplary deficiencies commonly associated with the prior art as described herein.

For example, certain exemplary embodiments of the present disclosure can provide exemplary visualization system, method, procedure, and computer-accessible medium, which can individually and/or collectively be called, e.g., IR. Exemplary embodiments of such exemplary IR can be used to compare two exemplary groups of objects with specific and distinguished exemplary properties. Such group can include exemplary case subjects with a particular exemplary disease, a group of exemplary control subjects without that particular exemplary disease, an exemplary group of subjects with a particular exemplary disease who are given an exemplary treatment, and/or an exemplary group of subjects with the same exemplary disease but under another exemplary treatment or no treatment at all.

According to certain exemplary embodiments of the present disclosure, an exemplary continuous scalar quantity, which can be called, e.g., a "risk score" can be assigned to each exemplary object and presented as an exemplary bar in an exemplary bar graph diagram. The exemplary risk score can have a magnitude which can be approximately proportional to a likelihood of belonging to an exemplary second group, which can mean that the exemplary objects from a first exemplary group can be assigned smaller exemplary risk scores, while exemplary objects from the second exemplary group can be assigned larger exemplary risk scores, for example. Further, exemplary risk score bars can: (a) be colored in different exemplary colors to represent the two exemplary groups of exemplary objects; (b) be sorted (e.g., ordered) by magnitude; and (c) plotted separately on different sides (e.g., left and right) of the same exemplary diagram to facilitate an exemplary visual comparison of the exemplary objects from the two exemplary groups.

The exemplary risk scores in certain exemplary embodiments of IR can be computed by an exemplary linear combination of exemplary predictor variables measured for each exemplary object. The exemplary predictor variables can include continuous quantities which can characterize inherent exemplary properties of the two exemplary groups of exemplary objects, such as binding of antibodies from human serum to a specific library of carbohydrates on a printed glycan array and/or gene expressions on a nucleic acid array, for example. The exemplary linear combination can be achieved by an exemplary set of exemplary coefficients that can be obtained by, e.g., known pattern recognition and statistical algorithms and/or procedures, such as, e.g., logistic regression, linear regression, linear discriminant analysis (e.g., which may be known as Fisher linear discriminant) and/or by an exemplary support vector machine, and an exemplary biased by an intercept term which can make an exemplary risk score negative for the most objects from the first exemplary group and positive for the most exemplary objects from the second group.

The exemplary risk scores can also be transformed by an exemplary monotonous function which can make them take the exemplary values between zero and one, where most of the exemplary transformed risk scores for the first exemplary group can have values smaller than approximately 0.5, while most of the exemplary transformed risk scores for the second exemplary group can have values of, e.g., between approximately 0.5 and approximately 1.0. For example, the exemplary transformed risk scores, in case of the exemplary combination of exemplary predictors obtained by exemplary logistic regression and transformed by exemplary sigmoid function (which can also be called, e.g., logistic function), can be proportional to an exemplary conditional probability of belonging to the second exemplary group.

According to certain exemplary embodiments, risk scores can also be alternatively computed as a natural logarithm of the ratio of distance measured between the object to the center of mass of the first group and the distance of the same object to the center of mass of the second group of objects, respectively. The exemplary distance measure can be obtained, e.g., as Mahalanobis distance and/or the Hotelling distance that can be determined for the predictor variables.

The exemplary risk score bars can be optionally rendered with two (or more) shades of the corresponding group color, such that the risk scores which have magnitudes that are within lower and upper quartiles can be rendered with a darker color shade, for example.

An exemplary diagram can include a horizontal cutoff line which can indicate, e.g., the line of zero risk scores or the line of, e.g., 0.5 value of monotonically transformed risk scores in exemplary embodiments including monotonic transformation risk scores. The risk scores can also be computed by, e.g., including in the linear combination of predictors the products of predictor variables, which are known in regression models as "interaction terms".

Certain exemplary embodiments in accordance with the present disclosure can also be used for, e.g., the classification of objects with unknown membership to one of two groups for which an IR can have previously been trained based on the same predictor variables and the same linear combination of predictor variables which can be used in the composition of a corresponding IR diagram, and measured for the particular object being classified. A bar which corresponds to the object of the unknown group membership being classified can be compared with bars of objects with known group membership, e.g., with a cutoff line. The bar which corresponds to the risk score of the object being classified can be rendered with a color which is different than the colors used for risk scores of the two groups of objects with known group membership that can be used to train an exemplary system, thus making the classification visually more convenient, for example.

The position of the cutoff line can be readjusted by, e.g., moving up and/or down the vertical axis of the IR diagram such that the classification of an object with unknown group membership can be modulated with a desired cost of misclassification of objects which belong to the first group versus the cost of misclassification of objects which belong to the second group. The readjustment of the cutoff line can be computed by using the specificity and sensitivity of the objects used to train the exemplary system and the desired ratio of the cost of false positive versus false negative rate.

Certain exemplary embodiments of IR in accordance with the present disclosure can be multifunctional in that they can be trained with multiple object group pairs provided that the predictor variables contain enough discriminative power for each pair of the group pairs. Thus, the classification of an object can be achieved with an unknown membership to any of the object groups used in the IR training. The measurement of the predictor variables for the object with the unknown group membership can be performed once, while the classification of the object with the unknown group membership can be performed via repeated classification procedures for, all, most or some of the object group pairs for which the exemplary IR is trained.

For example, exemplary IR can be trained with four pairs of patient groups, e.g.: (a) a group of subjects with breast cancer risk and a group of subjects with breast cancer, (b) a group of subjects with lung cancer risk and a group of subjects with lung cancer, (c) a group of subjects with ovarian cancer risk and a group of subjects with ovarian cancer, (d) a group of subjects with mesothelioma risk and a group of patients with mesothelioma. The predictor variables used in the IR training can be, e.g., signal intensities of anti-glycan antibodies binding to glycans on Printed Glycan Array (PGA), which can also called a "glyco-chip". The library of glycans which can be used in PGA may be large enough to cover all four exemplary cases (a) through (d) described in this example. For each such exemplary case, there can be a subset of glycans from the library that can provide enough discriminative power for all of the pairs of groups. A patient can come in for a medical check-up and/or cancer early-detection screening, both of which can be facilitated via a single drawing of the patient's blood. The patient's blood can be forwarded to a laboratory which can perform, e.g., serum extraction, incubation of the serum with the PGA, and scanning and preparation of data for the exemplary IR. A physician can run the same exemplary IR for four different cases to assess the health status of a patient. This multifunctional property of certain exemplary embodiments of IR and the PGA platform can eliminate the need for multiple tests and/or multiple patient visits, for example.

According to certain exemplary embodiments of the present disclosure, a computer-accessible medium having instructions thereon for comparing two groups of objects can be provided. For example, when a computing arrangement executes the instructions, the computing arrangement can be configured to execute the exemplary procedures. Such exemplary procedures can include assigning, to each of a plurality of objects, a scalar quantity that has a respective value, providing the scalar quantity assigned to each of the objects in a single diagram, and sorting the scalar quantities by respective magnitudes and grouping the scalar quantities according to the respective values thereof. Each of the values can be normalized to be between zero and one According to further exemplary embodiments of the present disclosure, the scalar quantities can include continuous scalar quantities, and can be sorted, for example, in an increasing numerical order of the respective values from a smallest value to a largest value. In addition, the scalar quantities can be grouped according to the respective values. and at least one of the scalar quantities can be provided as a bar in a bar graph, which can also include a cutoff line. The cutoff line can be determined as a function of the respective values. For example, the cutoff line can be determined using a specificity and/or a sensitivity of the objects.

According to yet additional exemplary embodiments of the present disclosure, the providing procedure can include assigning each bar with a particular color based the respective value of the corresponding scalar quantities. Further, each of the colors can correspond to one of the groups formed by the grouping procedure, and each of the bars representing a respective value within lower or upper quartiles of each of the groups can be assigned a particular shade of the color corresponding to the group. The scalar quantities can also be classified and assigned a bar representing a value associated with the classified scalar quantity with a color that can be different than a color associated with any of the groups generated by the grouping procedure.

In yet further exemplary embodiment of the present disclosure, the value of each of the scalar quantities can be determined by a linear combination of predictor variables associated with each of the objects, where the predictor variables can be continuous quantities which characterize at least one inherent property of each of the groups of the objects. Further, the predictor variables can be based on historical information associated with at least one of the objects so as to train the computing arrangement, and the inherent property can include (i) a binding characteristic of a type of antibodies from a human serum to a library of carbohydrates on a printed glycan array, and/or (ii) a gene expression on a nucleic acid array.

According to still another exemplary embodiment of the present disclosure, the linear combination can be determined using a set of coefficients obtained by (i) a logistic regression procedure, (ii) a linear regression procedure, (iii) a linear discriminant analysis procedure, and/or (iv) a support vector machine.

In still another exemplary embodiment of the present disclosure, each of the values can be adjusted to make the respective values negative for most of the objects of a first group of the groups, and to make the respective values positive for most of objects of a second group of the groups. For example, the values for most of the objects of the first group can be less than 0.5, and the respective values for most of the objects of the second group can be greater than 0.5.

According to another exemplary embodiment of the present disclosure. the respective value of each of the scalar quantities can be determined as a natural logarithm of a ratio of a first distance between the respective value of one of the objects to a center of mass of one group obtained by the grouping procedure, and second distance between the value of the one of the objects to a center of mass of another group obtained by the grouping procedure. The distance can be determined based on a Mahalanobis distance and/or a Hotelling distance.

In another exemplary embodiment of the present disclosure, a method for comparing two groups of objects can be provided. Using such exemplary method, it is possible to assign, to each of a plurality of objects, a scalar quantity that has a respective value, providing the scalar quantity assigned to each of the objects in a single diagram, and using a computing arrangement, sort the scalar quantities by respective magnitudes and grouping the scalar quantities according to the respective values thereof. It is also possible to display and/or store information associated with (i) the sorting of the scalar quantities, and/or (ii) the grouping of the scalar quantities, in a storage arrangement in a user-accessible format and/or a user-readable format.

In yet another exemplary embodiment of the present disclosure, a system for comparing two groups of objects can be provided. The exemplary system can include a computer-accessible medium having executable instructions thereon. For example, when at least one computing arrangement executes the instructions, the computing arrangement(s) can be configured to assign, to each of a plurality of objects, a scalar quantity that has a respective value, provide the scalar quantity assigned to each of the objects in a single diagram, and sort the scalar quantities by respective magnitudes and group the scalar quantities according to the respective values thereof.

These and other objects, features and advantages of the present invention will become apparent upon reading the following detailed description of exemplary embodiments of the present disclosure, when taken in conjunction with the accompanying exemplary drawings and appended claims.

BRIEF DESCRIPTION OF THE DRAWINGS

The foregoing and other objects of the present disclosure will be apparent upon consideration of the following detailed description, taken in conjunction with the accompanying exemplary drawings and claims showing illustrative embodiments of the invention, in which:

FIG. 11 is an illustration of a graph of another exemplary diagram in accordance with certain exemplary embodiments of the present disclosure;

FIG. 12 is an illustration of a graph of still another exemplary diagram in accordance with certain exemplary embodiments of the present disclosure;

FIG. 18 is an illustration of an exemplary block/flow diagram of an exemplary IR system in accordance with certain exemplary embodiments of the present disclosure;

FIG. 19 is another illustration of an exemplary block/flow diagram of an exemplary configuration in accordance with further exemplary embodiments of the present disclosure;

Figure 1:
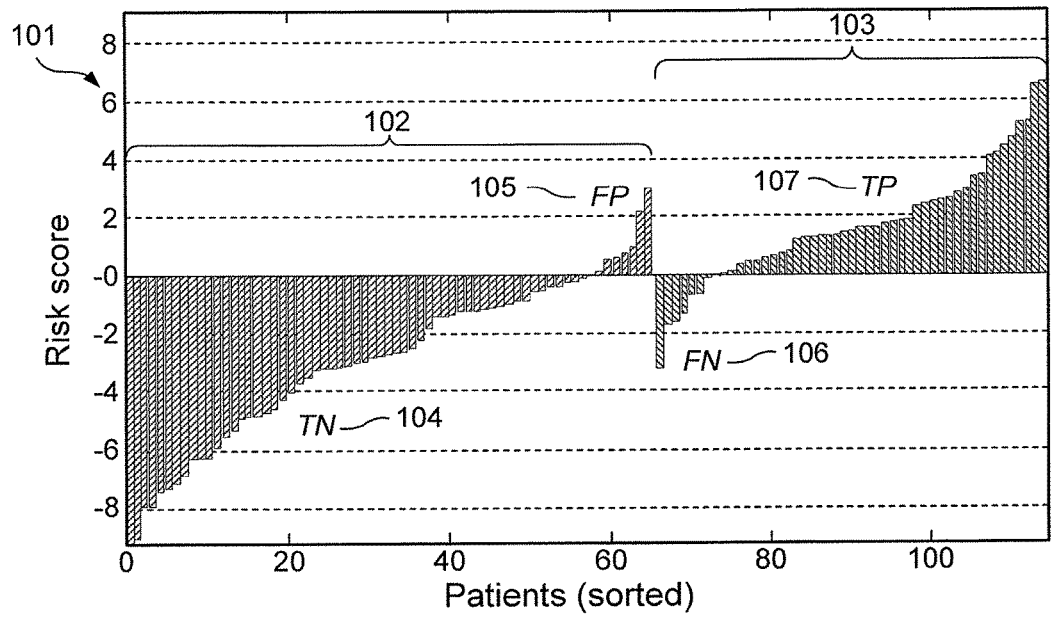
FIG. 1 is an illustration of a graph of an exemplary IR diagram with control and case values of exemplary risk scores in accordance with certain exemplary embodiments of the present disclosure.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure.

DETAILED DESCRIPTION OF EXEMPLARY EMBODIMENTS OF THE DISCLOSURE

Exemplary embodiments of the present disclosure can be implemented by the exemplary system, method, and/or computer-accessible medium in accordance with the present disclosure, which can be collectively and/or individually called, e.g., ImmunoRuler (IR).

For example, the exemplary IR can be, but not limited to, a set of exemplary procedures that can be integrated as a computer-based visual tool. The tool can, for example, provide for discovery and evaluation of glycan-based biomarkers, which can be used to discriminate, determine, distinguish and/or classify a high risk population from patients with malignancy and malignant patients with good and poor prognosis. Certain exemplary embodiments of IR can incorporate all, substantially all and/or a majority of bioinformatics information, including risk scores that can be generated by logistic regression, as well as other feature selection and classification algorithms and/or procedures. Exemplary embodiments of IR can provide, e.g., an easy-to-understand visualization of risk scores that can be associated with control and case samples from a physician's data repository of previously diagnosed/treated patients, as well as of new patients whom have not yet been diagnosed. This exemplary information can be used to assess a probability of patient(s) having an elevated cancer risk and/or a malignancy progression recurrence (e.g., early detection and diagnostic application), and/or to assess the survival probability (e.g., prognostic application).

Certain exemplary embodiments of IR can, e.g., support diagnostic and/or prognostic analysis of data obtained from Printed Glycan Arrays (PGA). For example, IR can provide a visual tool that can, e.g., be easily understood and used by medical doctors, nurses, and/or researchers in cancer biology, immunology and/or oncology. While most of the existing diagnostic tools can provide a limited range of diagnostic classification, the exemplary IR can determine an exemplary risk score of an undiagnosed patient, and present it graphically together with risk scores of already diagnosed patients from a clinical data repository. Such exemplary embodiments can, e.g., facilitate physicians to better estimate an exemplary level of a risk, and to compare it to levels of risk of other known patients. The exemplary IR also can incorporate other information that can be useful, such as, e.g., quartiles, medians, area under a ROC curve (AUC) and/or training precision, and the like.

By including diagnostic information (e.g., characteristics of different malignancies), IR can provide for the identification of patients potentially presenting with—or patients at-risk for, e.g., unexpected malignancies, for example, when utilized during medical check-ups and/or cancer early-detection screening. For example, exemplary embodiments of IR according to the present disclosure can provide for early detection of: (a) breast cancer and/or a breast cancer risk while screening for lung cancer and/or a lung cancer risk; (b) ovarian cancer and/or ovarian cancer risk while screening for breast cancer and/or a breast cancer risk; and/or (c) mesothelioma risk while screening for lung cancer and/or a lung cancer risk. Further, since certain exemplary embodiments of IR can be pre-trained (e.g., pre-configured, pre-programmed, etc.) for various pathologies and malignancy types, such exemplary embodiments of IR can be used to, e.g., screen/diagnose patients for various pathologies malignancies using a single (e.g., one) blood sample. This exemplary polymorphic feature of certain exemplary embodiments of the present disclosure can eliminate a need for multiple tests and/or multiple patient visits.

According to certain exemplary embodiments of the present disclosure, IR can be implemented as, e.g., a web-enabled application which can provide easy access to clinical data and/or performing patient screening, diagnosis and/or prognosis from remote locations via any networked computing arrangement, such as, a, desktop computer, a laptop, a notebook, a tablet, a smartphone, and/or mobile computers, personal digital assistants (PDAs), interactive television consoles, etc.

According to certain exemplary embodiments of the present disclosure, IR can include, e.g., an integrated collection of one or more procedures, computer-accessible medium and/or systems, as well as one or more exemplary visual tools, which can perform classifier training, testing of patients with unknown class membership (e.g., labels) and/or visualization of exemplary results. While certain exemplary embodiments of IR can be configured as an exemplary diagnostic and/or prognostic tool that can complement (e.g., can be compatible and work well with) an exemplary Printed Glycan Arrays (PGA) platform, certain exemplary embodiments of IR can also (or alternatively) be used in other areas of medicine, biology, and/or pattern recognition.

The name "ImmunoRuler" can also be configured to, e.g., process information that can include PGA data, which can be used to quantify a response of an immune system by measuring a level of binding of human antibodies against Tumor Associated Carbohydrates Antigens (TACA) and/or other glycans.

Exemplary embodiments of the system, method, procedure, and/or computer-accessible medium in accordance with the present disclosure can include, e.g., the following:

Exemplary Training Mode:

Input: Quantified raw PGA training data (e.g., physician's data repository), pre-processing parameters, feature selection methods, and classifier configuration;

Step 1: Data preprocessing (e.g., screening for noise, normalization, transformation and computation of quality control indicators, such as, e.g., Coefficient of variation, Concordance Correlation Coefficient (CCC), and Interclass Correlation Coefficient (ICC));

Step 2: Feature pre-filtering (e.g., selecting a subset of features which pass a univariate test, such as Wilcoxon-Mann-Whitney rank-sum test, with a desired p-value);

Step 3: Feature selection (e.g., selecting a specified number of features based on a configured univariate feature selection method, such as Wilcoxon-Mann-Whitney rank-sum test (WMW), or multivariate feature selection method, such as Forward Sequential Feature Selection (FSFS): Backward Sequential Feature Selection (BSFS), Stepwise Feature Selection (SFS), Classification and Regression Trees (CART), Random Forests, Markov Blankets, Genetic Algorithm (GA) and Ant Colony Optimization (ACO), etc.;

Step 4: Generation of the IR discriminant function (e.g., either by logistic regression, Generalized Linear Model (GLM), or by some other projection method such as Fisher Linear Discriminant (FLD), Support Vector Machine (SVM), linear regression etc. The discriminant function preferably depends on configured decision strategy/cutoff value which can be based on equal odds, middle of cluster centroids, ratio of the cost of false positive rate vs. false negative rate, etc.);

Step 5: Transformation of the linear discriminant into the risk score; There can be three definitions of risk scores used in IR (described herein): untransformed discriminant function, shifted discriminant function, and discriminant function transformed with sigmoid (logistic) function;

Step 6: Computation of IR-performance indicators, such as training precision, sensitivity, specificity, positive predictive value and the area under the ROC curve (AUC);

Step 7: (if requested): Computation of sensitivity functions of risk scores with respect to the binding level for various selected features (e.g., glycans); and Step 8: Plotting of a colored bar graph of sorted risk scores (e.g., risk scores can be separated into control and case group, and possibly the test samples).

Exemplary Classification/Test Mode:

Input: Quantified raw PGA data of patient(s) with unknown disease status. The exemplary IR can automatically retain the pre-processing parameters, selected features (e.g., signature), and classifier configuration obtained, for example, in training mode. The exemplary IR can also retain the data used for training.

Step 1: Removing features rejected by the screening process in training mode;

Step 2: Normalization and transformation of new data with the same parameters determined in training node;

Step 3: Extracting data that correspond to features selected in training mode, e.g., composing the design matrix;

Step 4: Computing the discriminant value(s) using the discriminant function generated in training mode;

Step 5: Computing the risk score; and

Step 6: Inserting the risk score(s) of test observations into IR diagram generated in training mode.

FIG. 1 shows an exemplary basic form of an exemplary IR diagram 101 with exemplary control and case values of exemplary risk scores, which can be represented by, e.g., bars 102 and 103, respectively. The exemplary values in this example can be obtained, received, measured, observed, determined, calculated, etc., and sorted by, e.g., increasing values of risk scores. Each of the bars shown in diagram 101 can represent a risk score, which, for example, can be an exemplary discriminant value as follows:

$$z_i = x_i^T w + w_o \quad (1)$$

where $x_i$ can represent an exemplary vector of, e.g., exemplary normalized and transformed binding intensities for exemplary patient i (e.g., i=1, 2, . . . , n) for selected exemplary features (e.g., glycans) that can generally include linear, interaction, and/or quadratic terms; w can represent an exemplary vector of exemplary logistic regression coefficients; and $w_o$ can represent an exemplary regression intercept coefficient. An exemplary class membership can be determined by, e.g., the sign of $z_i$, e.g., $z_i \leq 0$ can determine, classify, and/or designate exemplary control values (e.g., based on control observations), while $z_i > 0$ can determine, classify, and/or designate exemplary case values (e.g., based on case observations). Although in this example the projection vector w can be obtained by, e.g., multivariate logistic regression, certain exemplary embodiments of the present disclosure can provide for other projection methods, as described herein above.

As shown in FIG. 1, the exemplary IR can be plotted where control bars 102 and red bars 103 can represent, e.g., exemplary discriminant values $z_i$ for each subject in exemplary training samples. The exemplary diagram 101 can be obtained, e.g., by training an exemplary embodiment of IR with a mesothelioma assay (e.g., 65 asbestos exposed and 50 malignant mesothelioma).

In this example, an exemplary feature selection procedure can be performed, e.g., with an exemplary forward stepwise feature selection procedure, method and/or procedure (FSFS), and an exemplary projection vector can be obtained, e.g., utilizing an exemplary logistic regression procedure with an exemplary design matrix that contained four interaction terms. The exemplary interaction pairs of selected glycans can be, e.g., GID=(311, 121), (189, 507), (328, 121) and (121, 172). The resulting exemplary training precision can be approximately 87%, exemplary specificity can be approximately 89.2%, exemplary sensitivity can be approximately 84% and exemplary positive predictive value, e.g., can be approximately 85.7%, and the exemplary training AUC value can be approximately 0.924. In this example, exemplary contingency values, e.g., number of true negatives (TN) 104, false positives (FP) 105, false negatives (FN) 106, and true positives (TP) 107, are shown, for example, in a graph of the exemplary diagram 101 of FIG. 1.

In accordance with certain exemplary embodiments of the present disclosure, a solution of a larger number of exemplary interaction terms can result in, e.g., higher training precisions but with a potential consequence of overfitting. The utilization of four exemplary interaction terms can be considered as having provided the best unbiased cross-validation precision (e.g., over 75%) and therefore can have an expected minimal overfit. According to certain exemplary embodiments of the present disclosure, if more interaction and linear terms are selected, it can be preferable to use, e.g., larger training samples.

Figure 2:
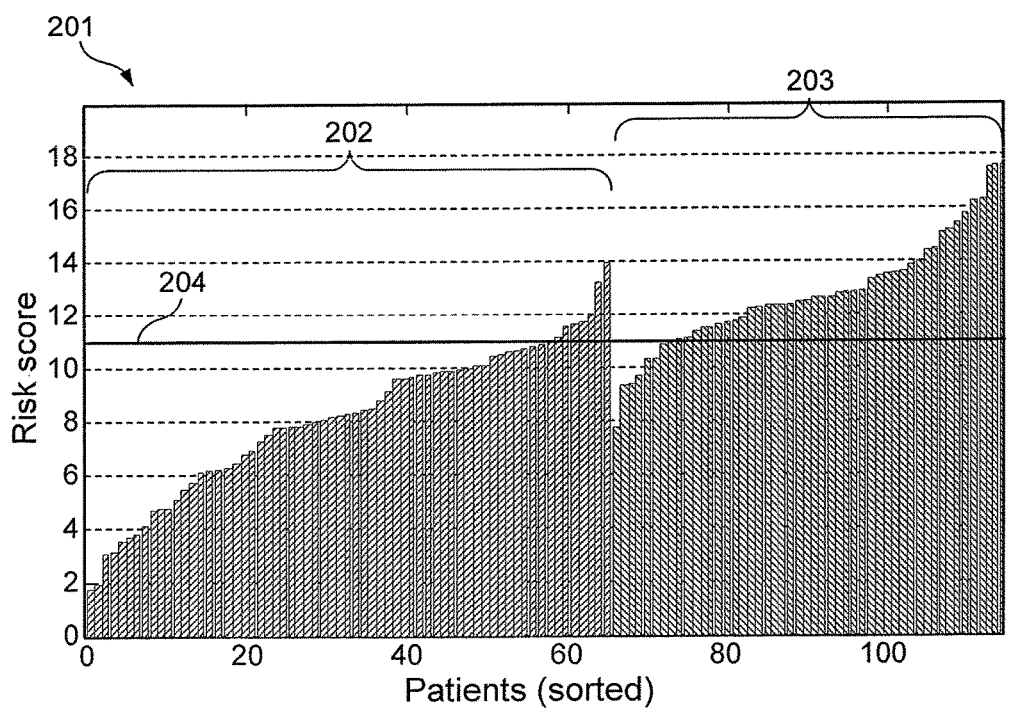
FIG. 2 is an illustration of a graph of another exemplary IR diagram in accordance with certain exemplary embodiments of the present disclosure.

FIG. 2 shows a graph of another exemplary basic IR diagram 201, which can be substantially similar to the exemplary diagram 101 of FIG. 1, except that the exemplary bars 102 and 103 of FIG. 1 are shifted upwards by, e.g., an exemplary constant value to make the values positive. This is shown in FIG. 2 by respectively corresponding exemplary bars 202 and 203. In accordance with certain exemplary embodiments of the present disclosure, it is possible to shift the exemplary bars (e.g., 102 and 103) upwards so that all bars (e.g., 202 and 203) are larger than an exemplary positive value.

Diagram 201 includes an exemplary horizontal line 204 that can represent an exemplary cutoff (e.g., decision) value, which, as in this example, can be determined by equal odds. According to certain exemplary embodiments of the present disclosure, the horizontal line 204 can be determined by other decision strategies, as described herein. As shown in FIG. 2, the exemplary bars of bars 202, for example, that are below exemplary horizontal line 204 can correspond to the true negative values 104 of FIG. 1, and the exemplary bars of bars 202 that extend above horizontal line 204 can correspond to the false positive values 105 of FIG. 1. Similarly, the exemplary bars of bars 203 that extend above exemplary horizontal line 204 can correspond to the true positive values 107 of FIG. 1, and the exemplary bars of bars 203 that are below horizontal line 204 can correspond to the false negative values 105 of FIG. 1.

Figure 3:
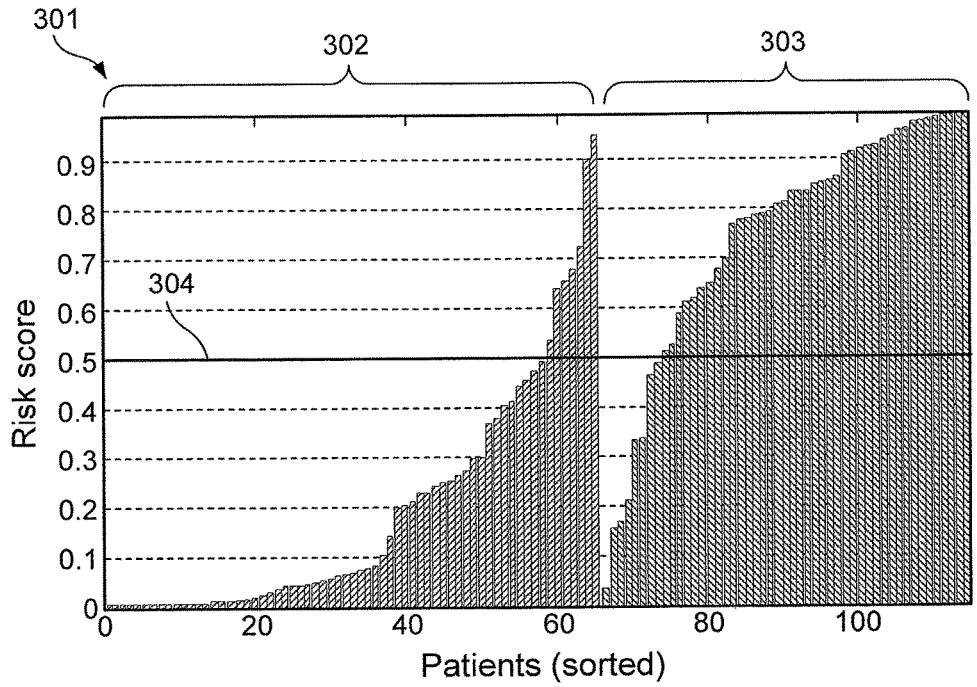
FIG. 3 is an illustration of a graph yet another IR diagram in accordance with certain exemplary embodiments of the present disclosure.

FIG. 3 shows a graph of still another exemplary IR diagram 301 in accordance with certain exemplary embodiments of the present disclosure, which can be substantially similar to the examples of FIGS. 1 and 2. However, the exemplary risk scores 302 and 303 shown in exemplary diagram 301 of FIG. 3, which can represent, e.g., exemplary control values and case values, respectively, can be obtained by transforming exemplary discriminant values through the following exemplary sigmoid (e.g., logistic) function:

$$r_i = \frac{e^{z_i}}{1+e^{z_i}} = \frac{1}{1+e^{-z_i}} \qquad (2)$$

For example, if exemplary projection vector w is obtained by logistic regression, the exemplary risk scores can have meaning of conditional probabilities Pr{Y∈case|X}, e.g., exemplary risk score $r_i$ can represent an exemplary probability that exemplary observation i can belong to an exemplary case sample.

An exemplary cutoff value, shown in the exemplary diagram 301 of FIG. 3 by exemplary horizontal line 304, can represent, e.g., the probability of approximately 0.5 (e.g., 50%) corresponding to equal odds of being a member of any of the samples. The exemplary cutoff line 304 can be moved up and down to achieve different proportion between specificities and sensitivities, as described herein. In addition to an exemplary benefit of, e.g., the exemplary meaningful interpretation of the exemplary risk scores 302 and 303 in case of logistic regression, this exemplary embodiment can standardize the exemplary risk score values 302 and 303 by limiting and/or conforming them to be within an exemplary range of e.g., [0, 1]. Thus, this example indicates that, e.g., the exemplary risk scores can be presented as all having values of, e.g., between 0 and 1. In an exemplary case of the projection based on logistic regression, the exemplary bars 302, 303 can represent, e.g., the conditional probabilities of belonging to an exemplary case sample.

As described herein, the risk scores that can be obtained by logistic regression and sigmoid transformation can represent the probabilities of the subject's membership to the case sample. This can also be applied to other linear projection methods and/or procedures, e.g., including FLD and SVM, if the sigmoid function is parameterized, for example, as follows:

$$r_i = \mathrm{Sigmoid}\left(\frac{z_i - m}{s}\right) \qquad (12)$$

where the parameters m and s can be obtained by maximizing the log-likelihood function:

$$L(m, s) = \sum_{i=1}^{n} [t_i \log(r_i) - (1 - t_i)\log(1 - r_i)] \qquad (13)$$

where $$t_i = \begin{cases} \dfrac{n_2+1}{n_2+2} & \text{for case observation} \\ \dfrac{1}{n_1+2} & \text{for control observation} \end{cases} \qquad (14)$$

And where $n_1$ and $n_2$ can be the control and case sample sizes. (See, e.g., Platt, J. C. (2000) "Probabilistic outputs for support vector machines and comparison to regularized likelihood methods", In: Smola, A, Barlet, P., Scholkopf, B. and Schuuramans, D. (Eds.) "Advances in Large Margin Classifiers", Cambridge, Mass., MIT Press) In certain exemplary embodiments of the present disclosure, a rapidly converging algorithm for finding the optimal values of m and s can be integrated with the exemplary IR.

According to certain exemplary embodiments of the present disclosure, further information can be added to exemplary IR. For example, each exemplary diagram can be accompanied an exemplary title which can show certain parameters that can be relevant to the IR training, such as, e.g., an exemplary feature selection method, a prefitering parameter, a projection method, selected features, regression coefficients (e.g., exemplary intercept coefficient $w_o$ and exemplary projection vector w), corresponding p-values for the coefficients, a decision strategy, a presentation type, a training precision, a specificity, a sensitivity and a positive predictive value, a training AUC value, a source of training data, a concentration, etc. An example of an exemplary title that can correspond to the exemplary diagram 101 illustrated in FIG. 1, is shown, for example, in FIG. 4.

Figure 4:
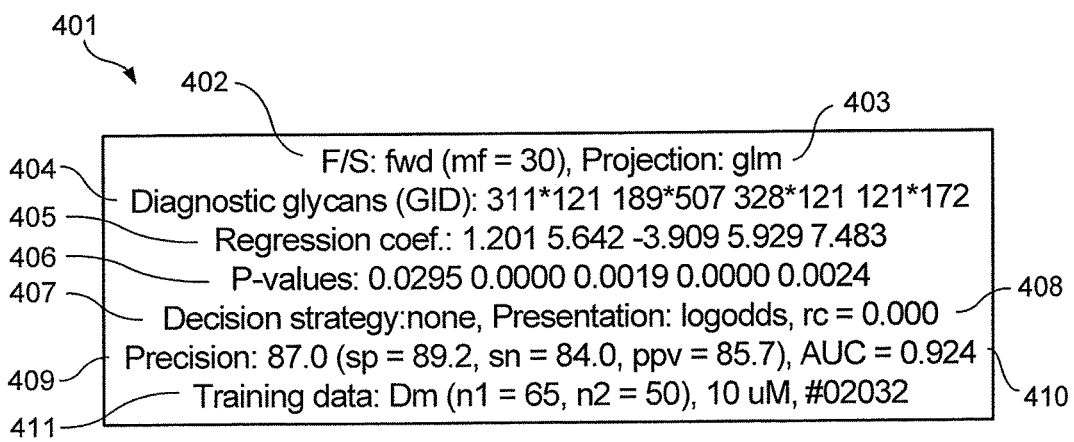
FIG. 4 is an illustration of an exemplary title block (e.g., a front matter) that can correspond to the exemplary IR diagram shown in FIG. 1 in accordance with certain exemplary embodiments of the present disclosure.

For example, FIG. 4 illustrates an exemplary title 401 (e.g., front matter) that can correspond do the exemplary diagram 101 illustrated in FIG. 1. As shown in FIG. 4, the exemplary title 401 can include certain exemplary parameters 402-411, which can include a feature selection method procedure 402, a projection method procedure 403, a diagnostic glycans (GID) 404, regression coefficients 405, p-values 406, decision strategy 407, presentation type 408, exemplary precision 409, exemplary AUC value 410, and a exemplary source of training data 411, for example.

According to certain exemplary embodiments of the present disclosure, the additional information which can be useful can be estimated (e.g., cross-validated) precisions and AUC values that can include, e.g., an exemplary confidence interval for an exemplary AUC value. These exemplary values, which can be optional in certain exemplary embodiments of the present disclosure, can involve additional computations and/or complex computations, and thus, possibly a longer computational time than may be involved with other exemplary embodiments of the present disclosure.

According to certain exemplary embodiments of the present disclosure, in order to relate exemplary risk scores (e.g., IR bars) to a particular patient from the exemplary training samples, the IR can be accompanied with, e.g., an exemplary list of patient identification numbers (PID), which can be sorted in the same manner as the risk score bars can be sorted. An example of an exemplary list, which can correspond to the three exemplary versions of IR illustrated in diagrams 101, 201, and 301 of FIGS. 1, 2, and 3, respectively, is provided in the following exemplary Table 1. For example, the exemplary patient PID=707 can correspond to the first (e.g., left-most) bar of the exemplary control bars 102, 202, and 302 in the exemplary diagrams 101, 201, and 301. Exemplary patient PID=711 can correspond to the last (e.g., right-most) bar of the exemplary control bars 102, 202, and 302. Exemplary patient PID=605 can correspond to the first (e.g., left-most) bar of the exemplary case bars 103, 203, and 303. Exemplary patient PID=361 can correspond to the last (e.g., right-most) bar of the exemplary case bars 103, 203, and 303 in exemplary the diagrams 101, 201, and 301.

TABLE 1

List of patients for each group:

Control Sample (65):

| | | | | | | | | | |
|---|---|---|---|---|---|---|---|---|---|
| 707, | 735, | 760, | 716, | 756, | 768, | 720, | 733, | 737, | 755 |
| 700, | 702, | 708, | 706, | 730, | 729, | 762, | 747, | 754, | 718 |

TABLE 1-continued

List of patients for each group:

| 713, | 705, | 721, | 743, | 739, | 725, | 764, | 775, | 704, | 738 |
|---|---|---|---|---|---|---|---|---|---|
| 740, | 710, | 734, | 750, | 766, | 748, | 719, | 759, | 771, | 717 |
| 712, | 765, | 763, | 728, | 736, | 701, | 732, | 749, | 770, | 767 |
| 744, | 731, | 714, | 774, | 741, | 769, | 745, | 772, | 758, | 715 |
| 709, | 746, | 810, | 757, | 711 | | | | | |

Case Sample (50):

| 605, | 307, | 158, | 78, | 621, | 125, | 647, | 143, | 866, | 509 |
|---|---|---|---|---|---|---|---|---|---|
| 107, | 278, | 317, | 529, | 145, | 59, | 523, | 494, | 322, | 49 |
| 887, | 294, | 194, | 337, | 259, | 112, | 251, | 291, | 258, | 149 |
| 133, | 144, | 132, | 128, | 331, | 312, | 272, | 172, | 79, | 519 |
| 440, | 347, | 636, | 298, | 184, | 313, | 168, | 99, | 179, | 361 |

According to certain exemplary embodiments of the present disclosure, an interactive version of IR can be provided in which exemplary bar values and exemplary PIDs can be obtained by selecting any of the bars (e.g., using a computer mouse, placing the on-screen pointer to a position over an exemplary particular bar and clicking a mouse button to select such exemplary particular bar). According to further exemplary embodiments of this present disclosure, a particular bar can be selected by using, e.g., a computer keyboard, touch-screen, etc.

Figure 22:
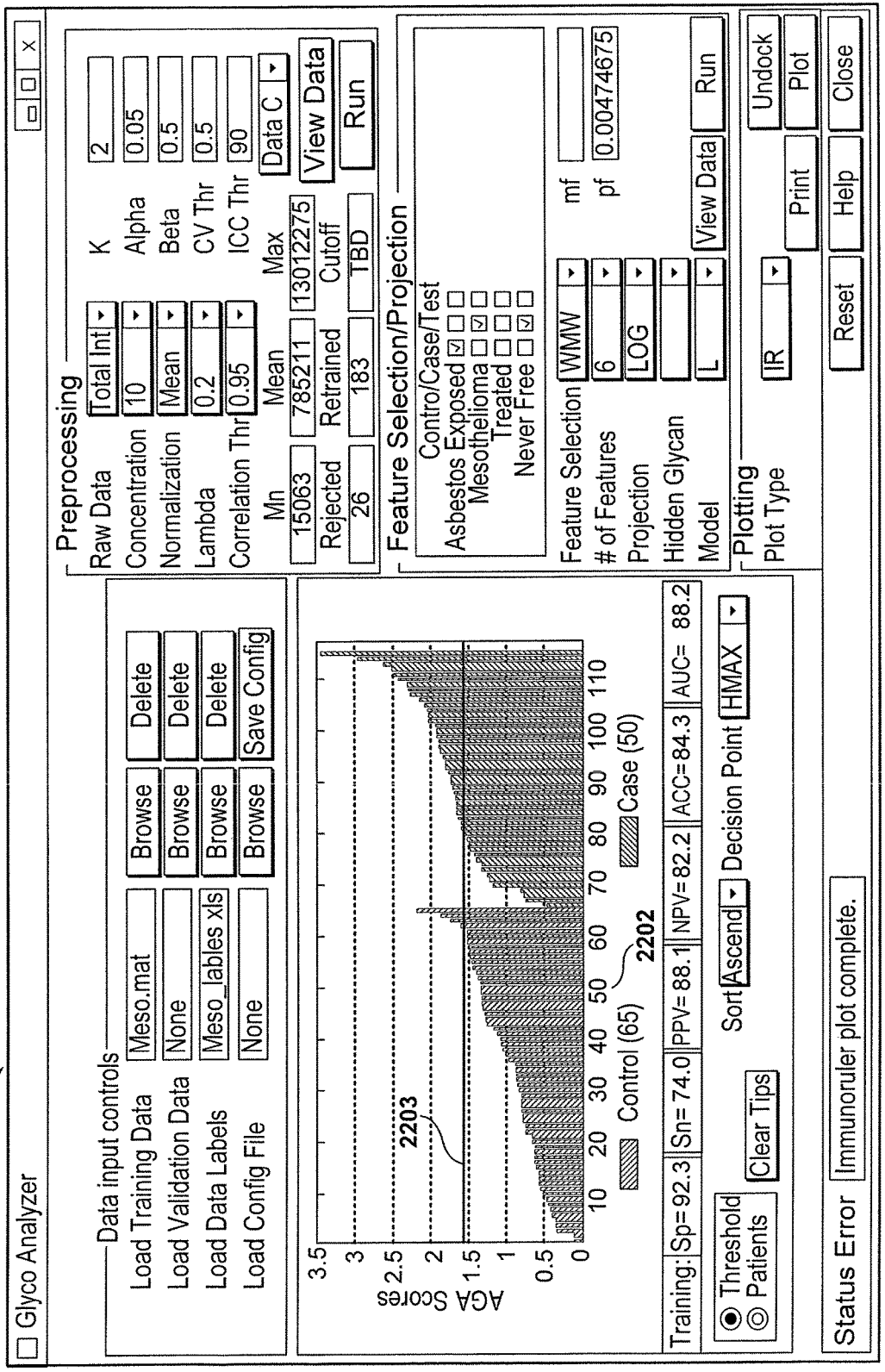
FIG. 22 is an illustration of an exemplary user interface of an exemplary configuration in accordance with certain exemplary embodiments of the present disclosure.

A snapshot of an exemplary the GUI 2201 is shown, for example, in FIG. 22. The exemplary software implementation, including the exemplary GUI 2201, can facilitate data entry and use of the exemplary IR by end-users who are not programmers. As shown in FIG. 22, the graphical pane 2202, for example, can display an exemplary IR diagram. The graphical pane 2202 can also display other types of diagrams, such as, e.g., a probability density function (pdf), box plots, and/or ROC curves. The exemplary IR diagram can be interactive in sense that clicking at a particular patient bar can cause display of the PID. In addition, the horizontal decision threshold line can be moved via an input device 2203, such as a mouse, or a touch screen, or a stylus, etc., up or down to change the decision strategy as described above.

According to additional exemplary embodiments of the present disclosure, in order to provide for increased contrast and/or visualization, the exemplary bars 102, 202, and 302 can be filled with the color blue and have black edges, and the exemplary bars 103, 203, and 303 can be filled with the color red and have black edges. Other colors and/or color combinations can also be used. Accordingly, it is possible that, in certain exemplary cases that can involve large samples, the exemplary black bar edges can dominate over the colors of the exemplary bars, which can render the bar colors to be effectively and/or substantially invisible. In such exemplary cases, the bar edges can be removed so that the colors can be visible.

Figure 5:
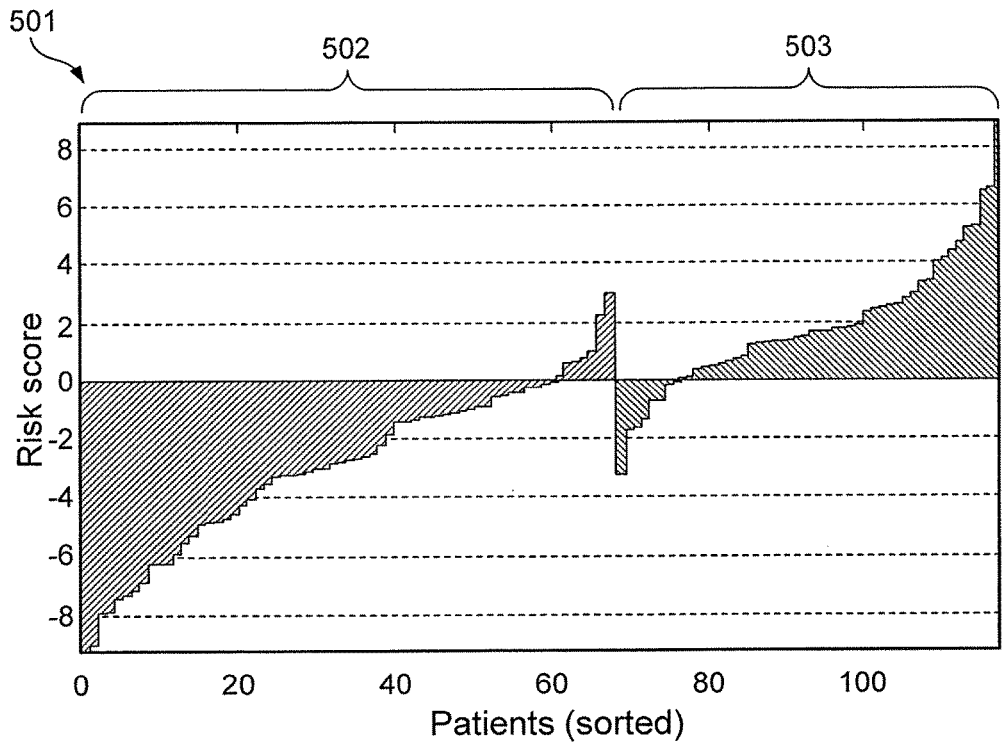
FIGS. 5-7 are illustrations of graphs of exemplary diagrams showing modified versions of the exemplary diagrams illustrated in FIGS. 1-3, respectively, in accordance with certain exemplary embodiments of the present disclosure.
Figure 6:
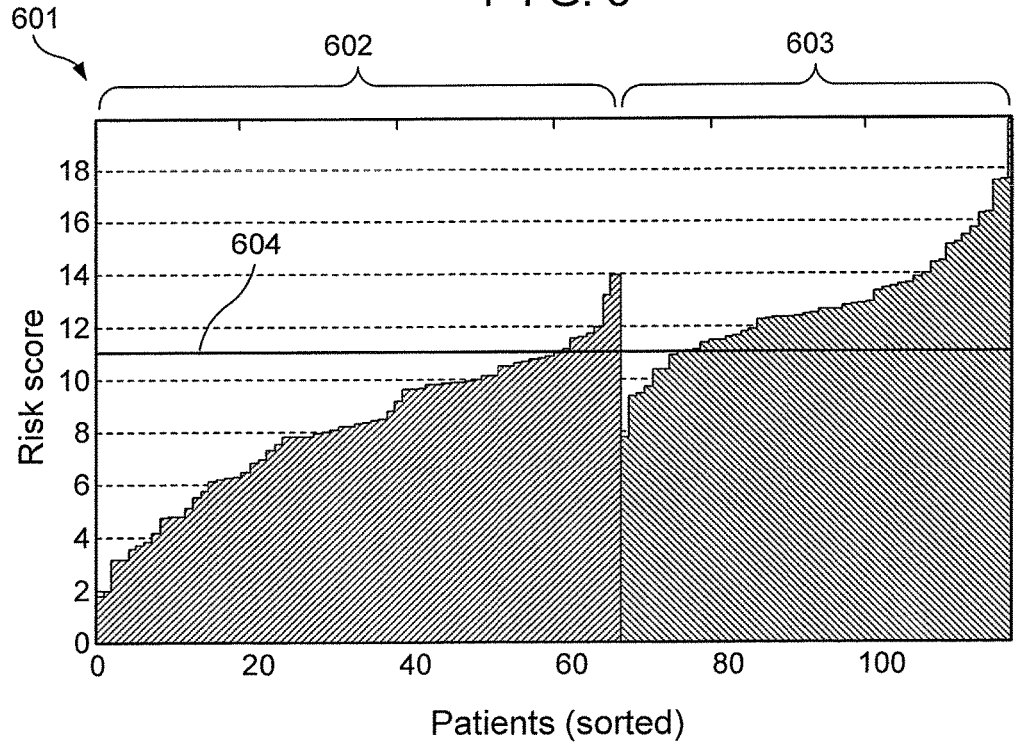
Figure 7:
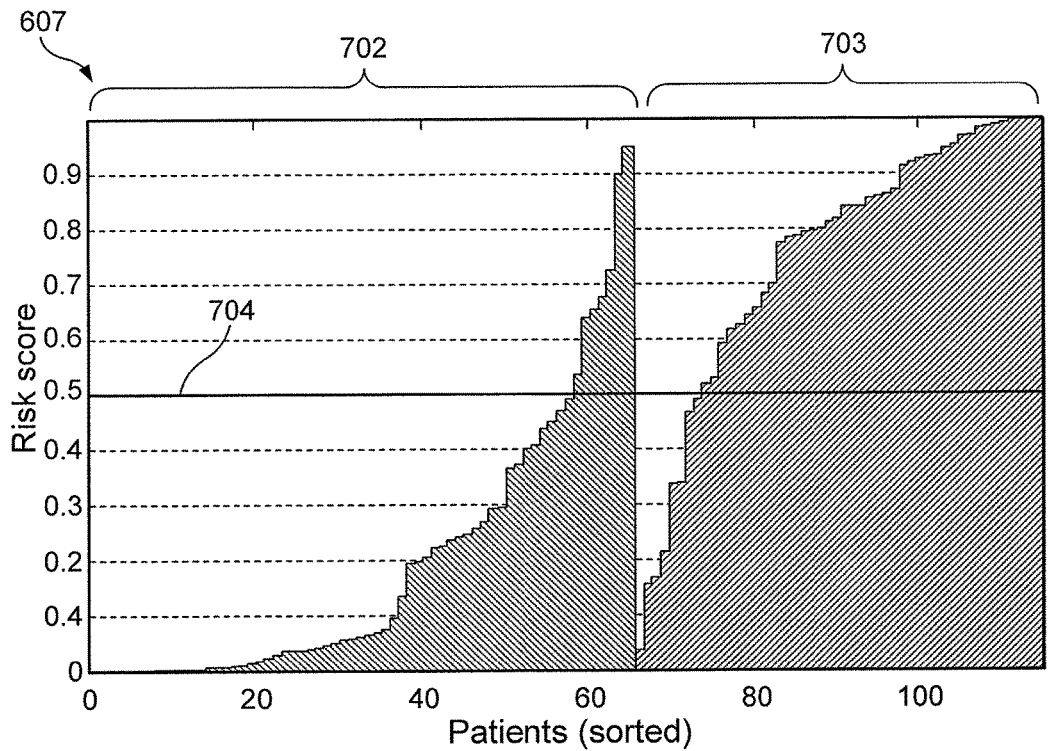

FIGS. 5, 6, and 7 show illustrations of graphs of exemplary diagrams 501, 601, and 701, respectively, which show exemplary results of removing the black bar edges from the bars of bars 102 and 103 of diagram 101, bars 202 and 203 of diagram 201, and bars 302 and 303 of diagram 301, respectively.

FIG. 5 shows an illustration of a graph of an exemplary diagram 501, which can be substantially the same as the diagram 101, except that the black bar edges of the bars 102 and 103 have been removed in the diagram 501, yielding exemplary bars 502 and 503.

FIG. 6 shows an illustration of a graph of an exemplary diagram 601, which can be substantially the same as the diagram 201, except that the black bar edges of the bars 202 and 203 have been removed in the diagram 601, yielding exemplary bars 602 and 603. Similarly, an exemplary horizontal line 604, as shown in FIG. 6, can correspond to the horizontal line 204 of FIG. 2.

FIG. 7 shows an illustration of a graph of an exemplary diagram 701, which can be the substantially the same as the diagram 301, except that the black bar edges of the bars 302 and 303 have been removed in the diagram 701, yielding exemplary bars 702 and 703. Similarly, an exemplary horizontal line 704 shown in FIG. 7 can correspond to the horizontal line 304 of FIG. 3.

According to certain exemplary embodiments of the present disclosure, an exemplary IR diagram can provide visible information about, e.g., quartiles of training samples, which can be available as a standard feature in box plots. For example, such information can be made visible by, e.g., brightening the color (or grayscale shade) of the exemplary bars of certain control and case samples, such that a darker color/shade can contain and/or represent exemplary observations, measurements, values, etc., which can be, e.g., within the 25 and 75 percentiles.

Figure 8:
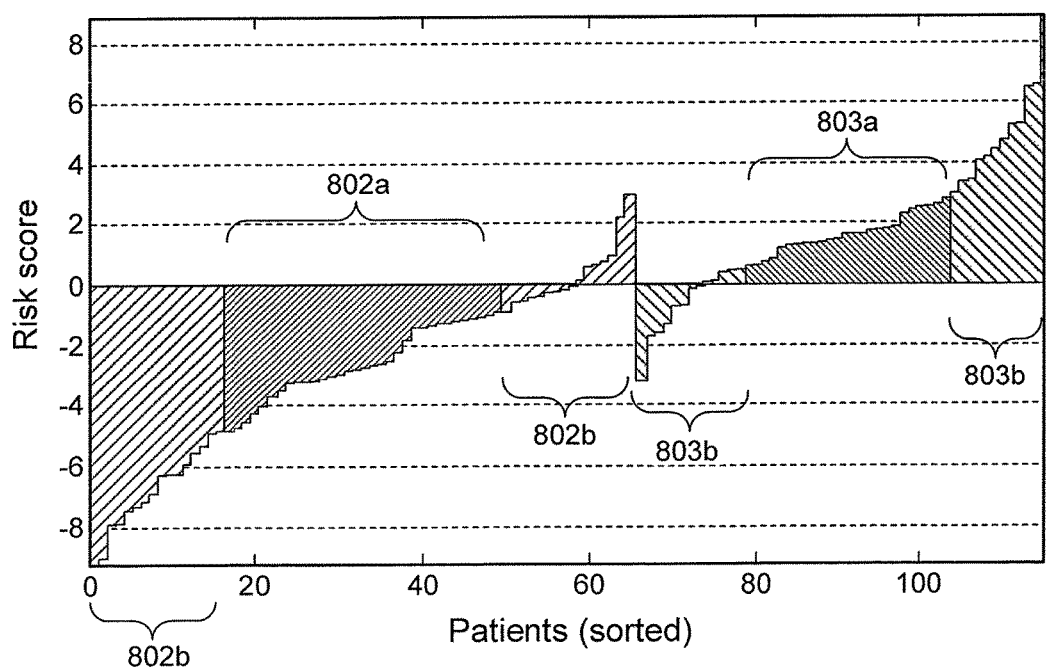
FIG. 8 is an illustration of a graph of another exemplary diagram in accordance with certain exemplary embodiments of the present disclosure.

FIG. 8 shows an illustration of a graph of an exemplary diagram 801, which can be substantially the same as the diagram 501 of FIG. 5. However, in this example, the bars 502 of FIG. 5 can correspond to exemplary bars 802*a* and 802*b* shown in FIG. 8 as, which can correspond to, e.g., the exemplary bars outside and inside of the exemplary 25-75 quartile box, respectively. Further, bars 803*a* and 803*b* of FIG. 8 can correspond to bars 503 of FIG. 5.

Figure 9:
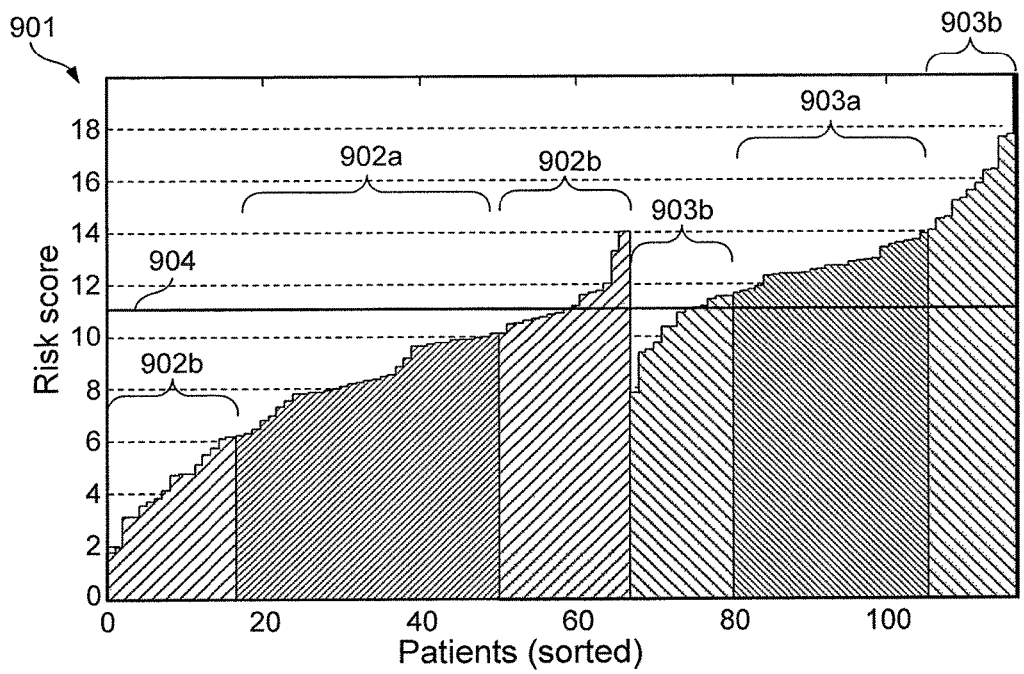
FIG. 9 is an illustration of a graph of yet another exemplary diagram in accordance with certain exemplary embodiments of the present disclosure.

FIG. 9 shows an illustration of a graph of still another exemplary diagram 901, which can be substantially the same as, e.g., the diagram 601 of FIG. 6. In this example, the bars 602 of FIG. 6 can correspond to exemplary bars 902*a* and 902*b* shown in FIG. 9, which can correspond to, e.g., the exemplary bars outside and inside of the exemplary 25-75 quartile box, respectively. Bars 903*a* and 903*b* of FIG. 9 can correspond to bars 603 of FIG. 6. Similarly, an exemplary horizontal line 904 shown in FIG. 9 can correspond to the horizontal line 604 of FIG. 6.

Figure 10:
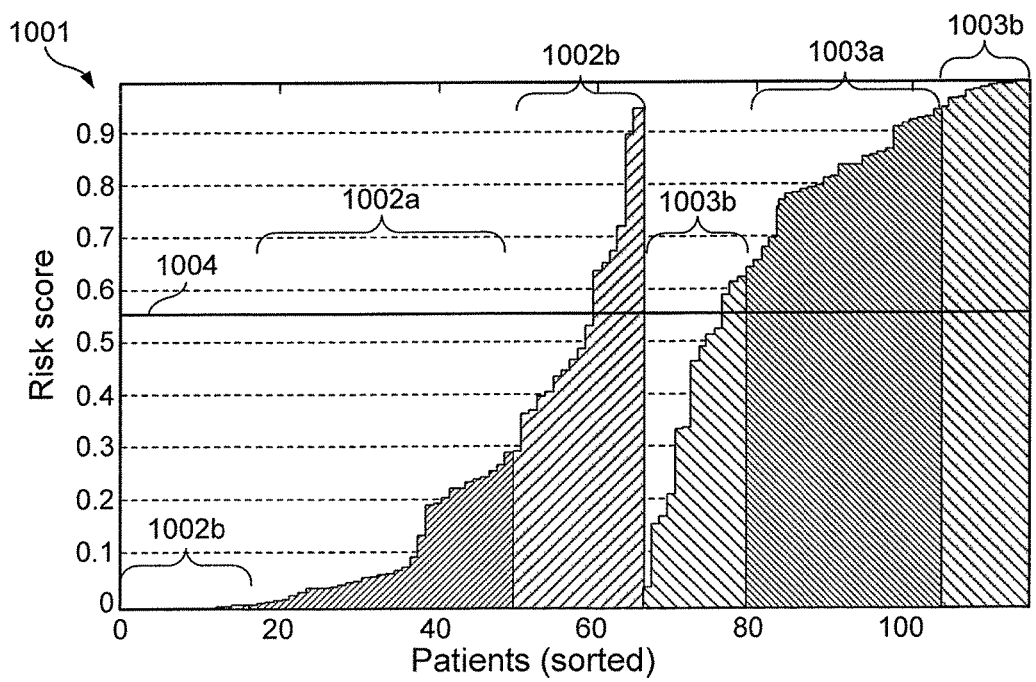
FIG. 10 is an illustration of a graph of yet another exemplary diagram in accordance with certain exemplary embodiments of the present disclosure.

FIG. 10 shows an illustration of a graph of an exemplary diagram 1001, which can be substantially the same as exemplary diagram 701 of FIG. 7. In this example, the bars 702 of FIG. 7 can correspond to exemplary bars 1002*a* and 1002*b* shown in FIG. 10, which can correspond to, e.g., the exemplary bars outside and inside of the exemplary 25-75 quartile box, respectively. Bars 1003*a* and 1003*b* of FIG. 10 can correspond to bars 703 of FIG. 7. Similarly, an exemplary horizontal line 1004 shown in FIG. 10 correspond to the horizontal line 704 of FIG. 7.

In accordance with certain exemplary embodiments of the present disclosure, IR can be configured and/or adapted to be used for or in, e.g., a particular exemplary application. For example, in an exemplary case of screening of an exemplary general population for breast cancer, where the prevalence of disease can be very low, it can be important to have a high exemplary specificity, while an exemplary sensitivity can be considered to be not important as long as it has values of, e.g., above approximately 40%, above approximately 45%, and/or above 50%. A low exemplary specificity can result in a higher amount of exemplary false positives, which can lead to, e.g., unnecessary requests for additional, more painful and more expensive tests such as mammograms or biopsies. Similarly, exemplary high sensitivity values can be preferable in accordance with certain exemplary embodiments of the present disclosure, such as, e.g., when used for in screening and the diagnosis of lung cancer among smokers and/or hereditary high risk patients.

Therefore, the exemplary IR in accordance with certain exemplary embodiments of the present disclosure can provide an exemplary provision of adjusting the decision cutoff value such that the exemplary IR can be configured for various decision strategies. For example, instead of (or in conjunction with) using an exemplary zero discriminant value or exemplary equal probabilities (e.g., $r_c$=0.5), a particular cutoff value which increases the sensitivity on account of specificity, or vice versa, can be used. The IR can, e.g., specify an exemplary ratio between exemplary costs of misclassification of controls (e.g., false positive rate (FPR)) and misclassification of cases (e.g., false negative rate (FNR)), which exemplary ratio can be expressed as, e.g.:

$$\gamma = \frac{C_{fpr}}{C_{fnr}} \quad (3)$$

Accordingly, an exemplary total cost of misclassification can be expressed as, e.g.:

$$C_{tot}=C_{fpr}FPR+C_{fnr}FNR=C_{fpr}(1-S_p)+C_{fnr}(1-S_n) \quad (4)$$

where $S_p$ and $S_n$ can represent specificity and sensitivity, respectively.

Since FPR, FNR, $S_p$ and $S_n$ can be functions of an exemplary decision threshold $r_c$, an exemplary optimal $r_o$ for an exemplary specified $\gamma$ can be obtained (and/or measured, received, determined, calculated, etc.) by maximizing the exemplary function:

$$J(r_c) = \gamma S_p(r_c) + S_n(r_c), \text{ e.g.} \quad (5)$$

$$r_o = \underset{r_c}{\mathrm{argmax}}\{J(r_c)\} \quad (6)$$

An exemplary IR system, method and/or procedure can, e.g., include an exemplary maximization procedure (e.g., exemplary Equation 6). Exemplary illustrations are provided in FIGS. 11 and 12 for two exemplary cost ratios, $\gamma$=1/3 and $\gamma$=3/1, respectively.

In particular, FIG. 11 shows an illustration of a graph of still another exemplary diagram 1101, which can be substantially similar to the diagram 901 illustrated in FIG. 9. The exemplary IR shown in FIG. 11 can be substantially the same as the exemplary IR for FIG. 9. For example, exemplary risk score values 1102 and 1103 can be substantially the same as the risk score values 902 and 903 of FIG. 9, respectively. However, as shown by the example of FIG. 11, an exemplary decision cutoff value 1104 can be different than the cutoff value 904 of FIG. 9. For example, the cutoff value 1104 can be determined by, e.g., setting an exemplary cost of misclassification of cases to be three times larger than the cost of the misclassification of controls. As a result, the exemplary sensitivity can be increased from approximately 84% to approximately 92%. A consequence can be, e.g., that an exemplary specificity can drop from approximately 89% to approximately 77%, for example.

FIG. 12 shown an illustration of a graph of another exemplary diagram 1201, which also can be substantially similar to the exemplary diagram 901 illustrated in FIG. 9. Thus, the exemplary IR of FIG. 12 also can be substantially the same as the IR of FIG. 9. For example, exemplary risk score values 1202 and 1203 can be substantially the same as the risk score values 902 and 903 of FIG. 9, respectively. However, as shown in the example of FIG. 12, an exemplary decision cutoff value 1204 can be different than the exemplary cutoff value 904 of FIG. 9. For example, the exemplary cutoff value 1204 can be determined by setting an exemplary cost of misclassification of cases to be, e.g., three times smaller than the cost of the misclassification of controls. As a result, the exemplary sensitivity can be increased from, e.g., approximately 89% to approximately 97%. A consequence can be, e.g., that an exemplary specificity can drop from approximately 84% to approximately 66%, for example.

As shown in the example of FIGS. 11 and 12, the exemplary IRs bars 1102 and 1103, and 1202 and 1203, respectively, can be shown with shifted bars. Substantially the same exemplary procedures for, e.g., shifting an exemplary cutoff value can be performed with other types of exemplary IR, exemplary direct discriminant functions (e.g., logarithm of odds) and/or exemplary probabilities (e.g., sigmoid transformation).

Certain exemplary embodiments can provide an exemplary IR to test unlabeled observations, measurements, etc., in patients with an unknown health status. For example, FIGS. 13-17 show illustrations of exemplary diagrams 1301, 1401, 1501, 1601, and 1701, respectively, which can be, e.g., substantially the same trained IR to one another but with additionally projected subjects having various levels of an exemplary risk score. The horizontal location of the corresponding bars 1305, 1405, 1505, 1605, 1705 within the exemplary diagrams 1301, 1401, 1501, 1601, 1701, respectively, can be adjusted to reflect an exemplary risk score level for the convenience of exemplary IR users.

The projected risk scores of e.g., test observations, measurements, etc., can be furnished with exemplary whiskers, e.g., 1306, 1406, 1506, 1606 and 1706, as shown in FIGS. 13-17, respectively. These illustrations can indicate an exemplary variation of the exemplary risk scores due to, e.g., an exemplary variation in an exemplary measurement of binding intensities on an exemplary printed glycans array. An exemplary measurement error can be tractable through the variation of replicates. Since averaging of exemplary replicated PGA signals can be done through an exemplary median of replicates, lower and upper values of an exemplary raw intensity for patient i and glycan j can be defined as, e.g.:

$$\tilde{x}_{ij}^L = \tilde{x}_{ij} - \delta_{ij}; \tilde{x}_{ij}^U = \tilde{x}_{ij} - \delta_{ij} \quad (7)$$

where $\tilde{x}_{ij}$ and $\delta_{ij}$ can represent a median and a median absolute deviation (MAD) across (and/or substantially all and/or a majority of) the exemplary replicates for subject i and glycan j, respectively (e.g., the exemplary tilde located above x can denote an exemplary raw signal). Exemplary signals $\tilde{x}_{ij}$, $\tilde{x}_{ij}^L$ and $\tilde{x}_{ij}^U$ can be subjected to an exemplary normalization procedure and/or an exemplary transformation procedure, and become, e.g., $x_{ij}$, $x_{ij}^L$ and $x_{ij}^U$, respectively. According to certain exemplary embodiments of the present disclosure, these exemplary signals can be considered in a context of m selected features, and each measurement can be represented as, e.g., an exemplary m-dimensional hypercube in m-dimensional feature space, where the vertices in dimension j can be, e.g., $x_{ij}^L$ and $x_{ij}^U$, while the center of the hypercube can be, e.g., vector $x_i$=($x_{i1}$, $x_{i2}$, . . . , $x_{im}$). A projection of this hypercube by an exemplary projection vector w, such as, exemplary regression coefficients $w_j$=0, 1, . . . , m, can provide exemplary $2^m$ projected values for each exemplary patient, $z_{ik}$, k=1, 2, . . . , $2^m$.

Exemplary lower and upper values for variation whiskers 1306, 1406, 1506, 1606, 1706 can be computed (and/or determined, calculated, processed, etc.) as, e.g.:

$$z_i^L = \min_k\{z_{ik}\}; z_i^U = \max_k\{z_{ik}\}; \qquad (8)$$

while an exemplary projection of an exemplary center of the hypercube can yield, e.g., value $z_i$ which can be used in exemplary Equation (1). Exemplary final risk scores $r_i^L$ and $r_i^U$ which can be shown as the variation whiskers 1306, 1406, 1506, 1606 and 1706 in the diagrams 1301-1701, respectively, can be obtained directly, through shifting and/or through sigmoid transformation of, e.g., $z_i^L$ and $z_i^U$, depending on the type of exemplary IR. Such exemplary described procedure can be implemented as a part of the exemplary IR in accordance with certain exemplary embodiments of the present disclosure.

Figure 13:
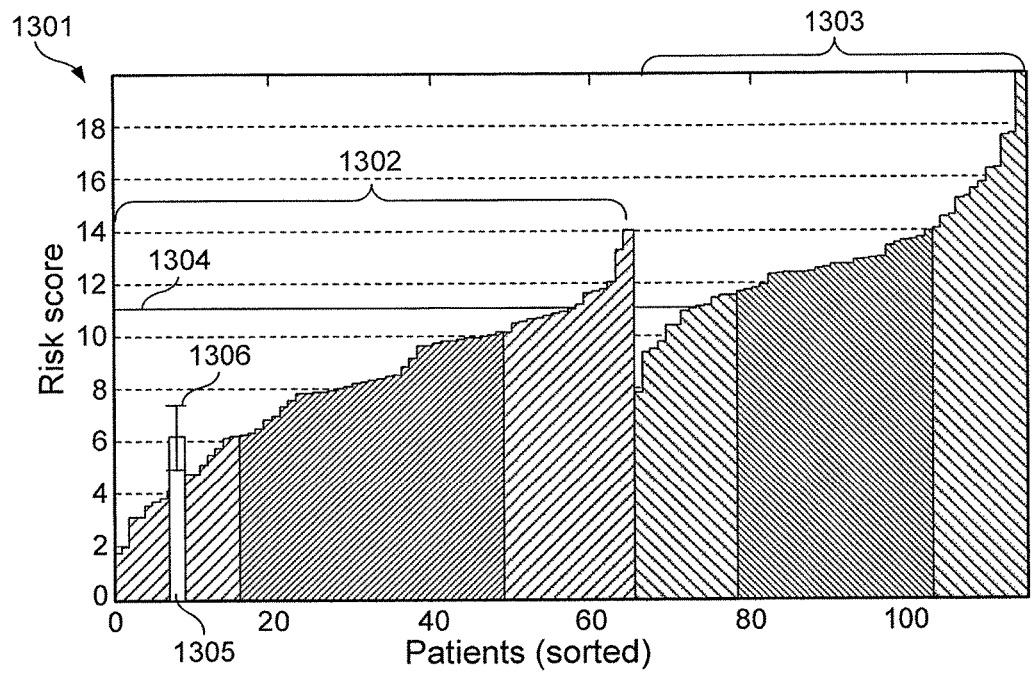
FIGS. 13-17 are further illustrations of graphs of exemplary diagrams in accordance with certain exemplary embodiments of the present disclosure.

As described herein above, for example, FIG. 13 shows an exemplary illustration of a graph of the exemplary diagram 1301, which can be based on substantially the same IR as that of FIG. 9, with an exemplary inserted risk score 1305 for an unlabeled patient. The risk score 1305 of the patient can be computed by using, e.g., the exemplary glycans and exemplary projection vector as determined in the IR training mode, for example. According to the diagram 1301, the patient can be classified as healthy. The whiskers 1306 can show an exemplary variation of the risk score 1305 of the unlabeled patient, which can be due to, e.g., a variation of an exemplary measurement error based on median bounds of the replicates.

Figure 14:
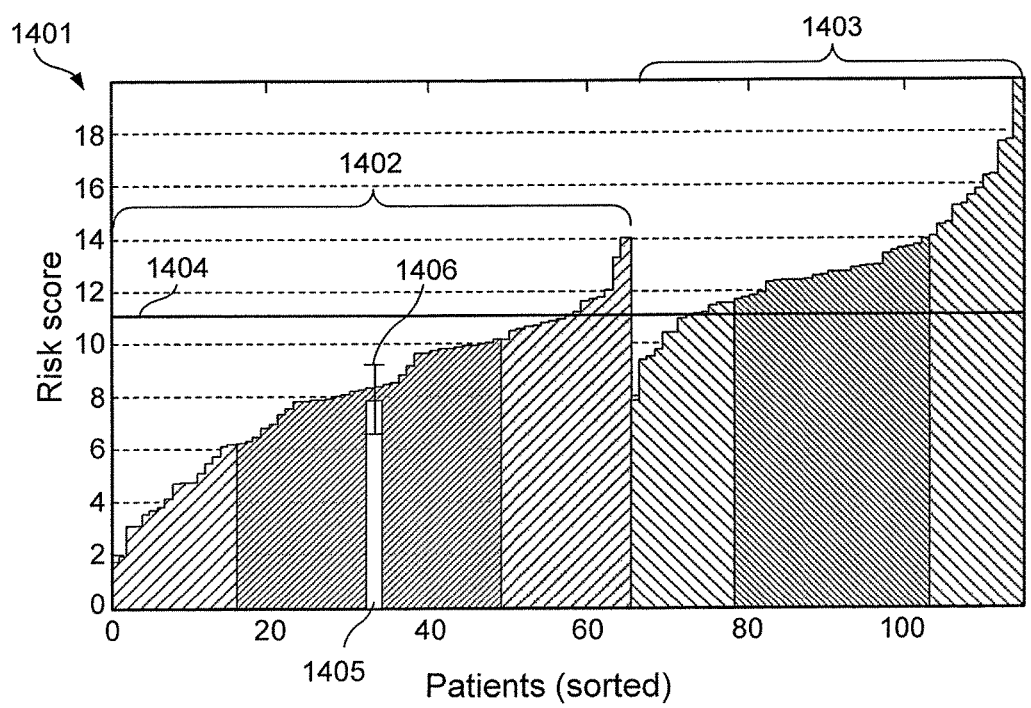

FIG. 14 shows an illustration a graph that is substantially the same as the illustration of FIG. 13, except that a different exemplary unlabeled patient with a larger exemplary risk score can be inserted into the exemplary IR. As also shown in this example of FIG. 14, an exemplary location of the patient's bar (e.g., 1405) can be located within an exemplary quartile box of an exemplary control sample, which can reflect its level of the risk score.

Figure 15:
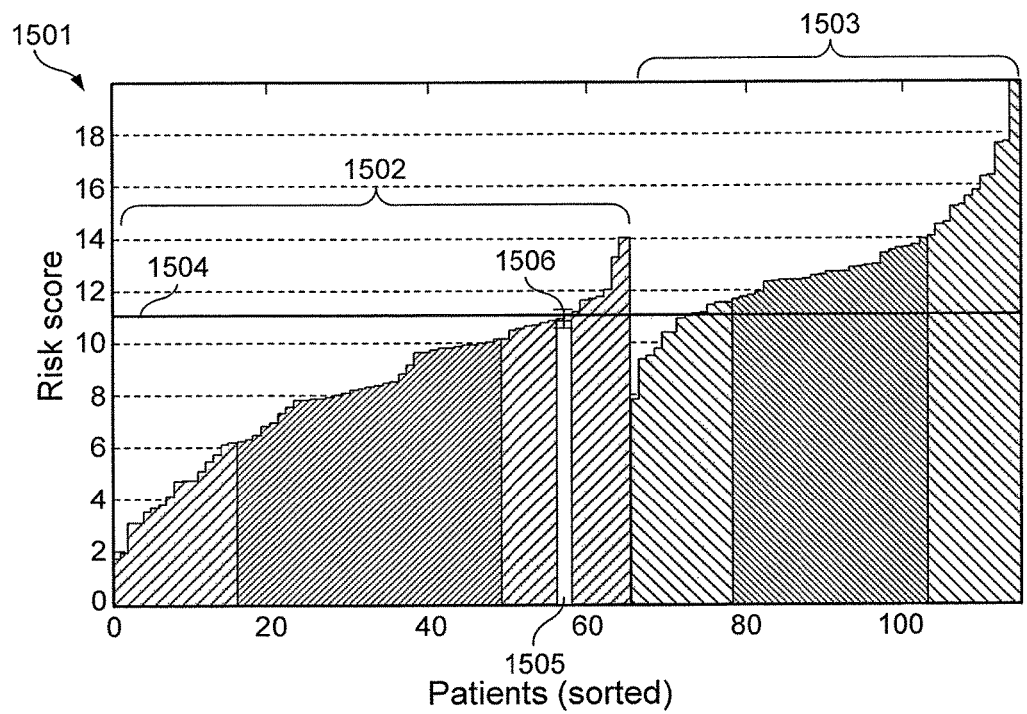

FIG. 15 shows an illustration of a graph that is substantially the same as, e.g., the illustrations of FIGS. 13 and 14, except that, as shown in FIG. 15, an exemplary projection of a different exemplary unlabeled patient with yet a higher exemplary risk score 1505 can be inserted into the IR. As also shown in this example, a patient can be in the upper end of the quartile box, and can thus be diagnosed with caution.

Figure 16:
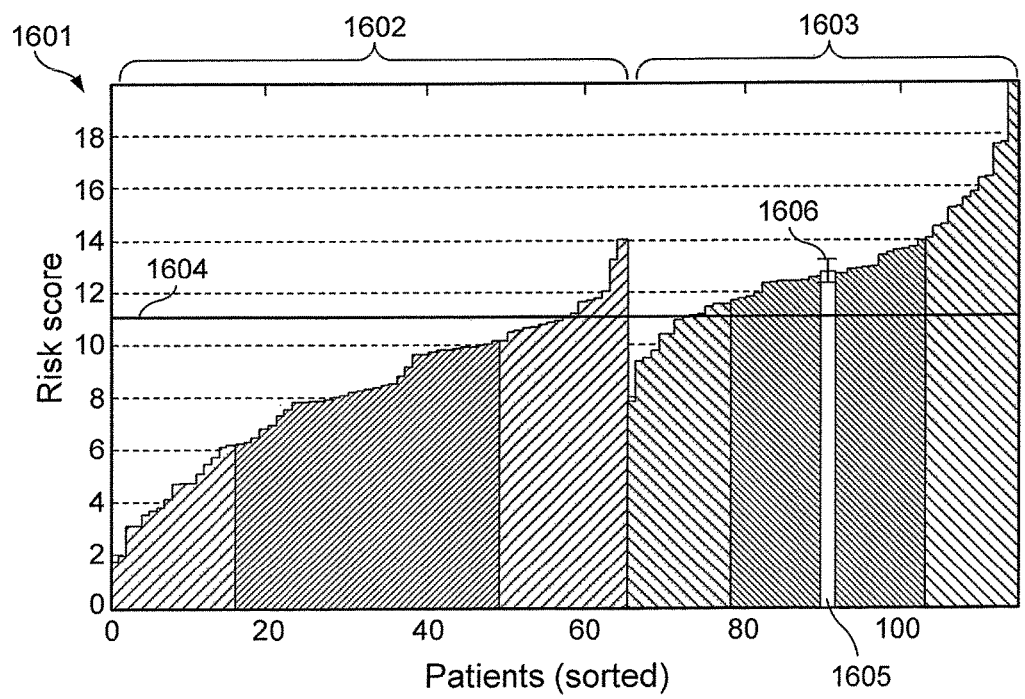

FIG. 16 shows an illustration of a graph that is substantially the same as, e.g., the illustrations of FIGS. 13-15, except that, as shown in FIG. 16, an exemplary projection of a different unlabeled patient with even a higher exemplary risk score 1605 can be inserted into the exemplary IR. The projected unlabeled patient of this example can be classified as malignant.

Figure 17:
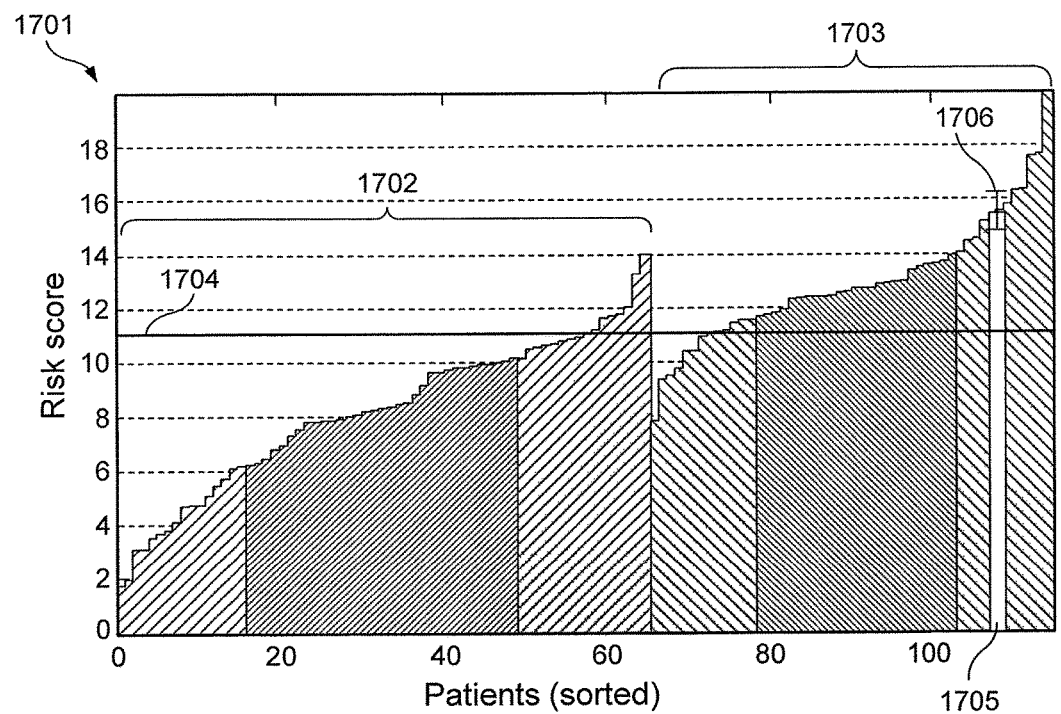

FIG. 17 shows an illustration of a graph that substantially the same as, e.g., the illustrations of FIGS. 13-16, except that, as shown in FIG. 17, an exemplary projection of a different unlabeled patient with an even higher exemplary risk score 1705 can be inserted into the exemplary IR. Accordingly, the projected unlabeled patient of this example can also be classified as malignant.

The exemplary embodiments of IR can have an additional exemplary provision such as, e.g., exemplary sensitivities of exemplary risk scores $r_1$ with respect to exemplary binding intensities for particular glycan, $x_{ij}$:

$$s_{ij} = \frac{\partial r_i}{\partial x_{ij}}. \qquad (9)$$

From exemplary Equations 1 and 2, described herein above, it follows that:

$$S_{ij}=w_j r_i(1-r_i). \qquad (10)$$

In accordance with certain exemplary embodiments of the present disclosure, a more practical form of sensitivity can be, e.g., relative sensitivity, which can show and/or provide, e.g., an exemplary relative change of an exemplary risk score caused by the relative change of an exemplary binding intensity, e.g.:

$$s_{ij} = \lim_{\Delta x_{ij}\to 0} \frac{\frac{\Delta r_i}{r_i}}{\frac{\Delta x_{ij}}{x_{ij}}} = \qquad (11)$$

$$\lim_{\Delta x_{ij}\to 0} \frac{\Delta r_i}{\Delta x_{ij}} \frac{x_{ij}}{r_i} = \frac{\partial r_i}{\partial x_{ij}} \frac{x_{ij}}{r_i} = S_{ij}\frac{x_{ij}}{r_i} = S_{ij}\frac{x_{ij}}{r_i} = w_j x_{ij}(1-r_i).$$

For example, $s_{ij}=4$ can mean that an approximately 1% increase of $x_{ij}$ can cause an approximately 4% increase in $r_i$.

FIG. 18 shows an exemplary illustration of a block/flow diagram 1801 according to an exemplary embodiment of the present disclosure which shows, e.g., an exemplary usage of an exemplary IR for early detection and diagnosis of cancer, for example. As shown in FIG. 18, information associated with a serum bank of control case subjects 1802 can be used in, e.g., the development, scanning, quantification and pre-processing 1803 of further information for training IR 1805. Such further information can be stored in, e.g., a PGA repository 1805 and/or used to generate a corresponding exemplary graph 1806. As also shown in FIG. 18, information associated with a serum of a new patient with an unknown health status 1807 can be used in, e.g., the development, scanning, quantification and preprocessing 1808 of further information that can be used by an exemplary embodiment of IR for a classification 1809 of the information associated with the new patient based on the trained IR 1805. Such further information and classification can be used to generate an exemplary graph 1810, which can include a bar 1811 that can represent a risk value associated with the new patient, for example.

FIG. 19 shows an exemplary illustration of another block/flow diagram 1901 of another exemplary embodiment of the present disclosure which shows an exemplary usage of an exemplary IR for, e.g., prognosis of cancer patients. As shown in FIG. 19, for example, clinical data in a database 1902 can be used for partitioning of Mesothelioma patients by month-to-death 1903 for training IR 1904, which can be done using information from a PGA data repository 1905. A Kaplan-Meier estimator 1906 can then be generated from the trained IR 1904. As also shown in FIG. 19, information associated with a serum of a new patient with an unknown health status 1907 can be used in, e.g., the development, scanning, quantification and preprocessing 1908 of further information that can be used by an exemplary embodiment of IR for a classification 1909 of the information associated with the new patient based on the trained IR 1904. Using the Kaplan-Meier estimator 1906 and classification 1909, it is possible to, e.g., generate an exemplary graph 1910 of month-to-death versus survival, thus providing exemplary resulting regions that can correspond to a good prognosis and/or a poor prognosis, as indicated by lines 1911 and 1912, respectively.

Figure 20:
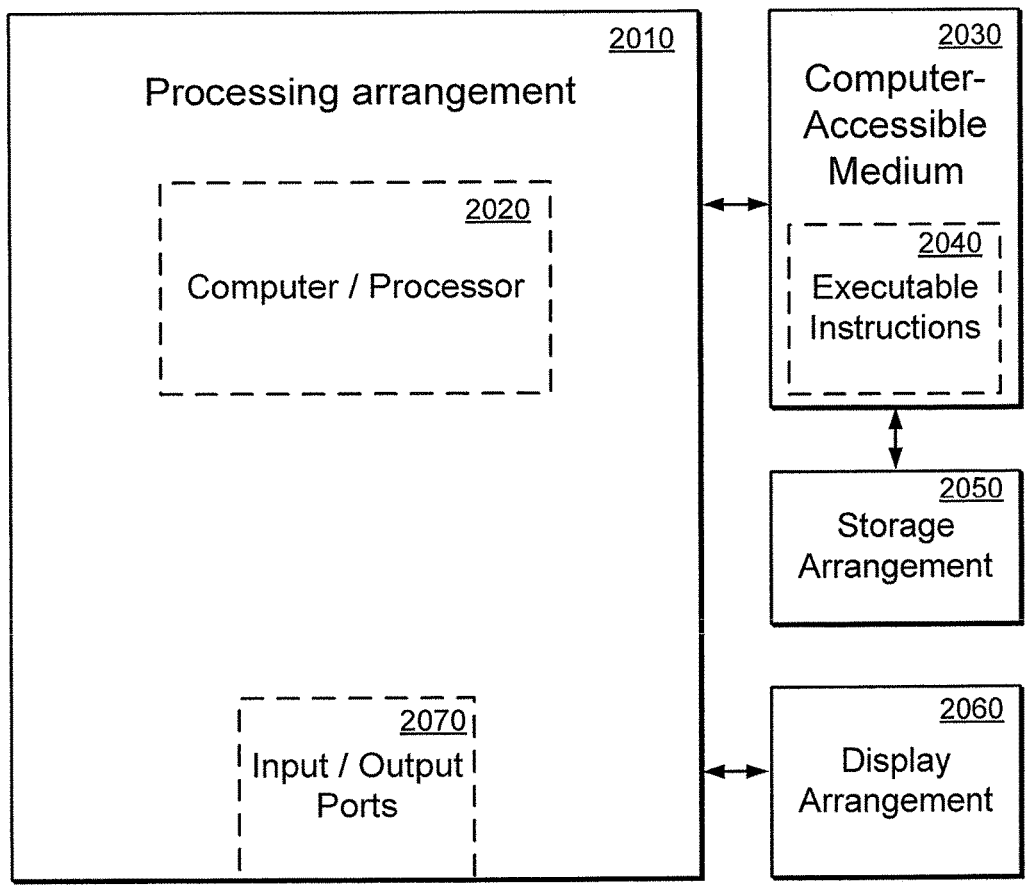
FIG. 20 is an illustration of an exemplary block diagram of an exemplary system in accordance with certain exemplary embodiments of the present disclosure.

FIG. 20 shows an exemplary illustration of an exemplary block diagram of an exemplary embodiment of a system according to the present disclosure for implementing certain exemplary IRs of the present disclosure. For example, an exemplary procedure in accordance with the present disclosure can be performed by a processing arrangement or a computing arrangement 2010. The processing arrangement 2010 can be, e.g., entirely or a part of, or include, but not limited to, a computer/processor 2020 that can include, e.g., one or more microprocessors, and use instructions stored on a computer-accessible medium (e.g., RAM, ROM, hard drive, or other storage device).

As shown in FIG. 20, e.g., a computer-accessible medium 2030 (e.g., as described herein above, a storage device such as a hard disk, floppy disk, memory stick, CD-ROM, RAM, ROM, etc., or a collection thereof) can be provided (e.g., in communication with the processing arrangement 2010). The computer-accessible medium 2030 can contain executable instructions 2040 thereon. In addition or alternatively, a storage arrangement 2050 can be provided separately from the computer-accessible medium 2030, which can provide the instructions to the processing arrangement 2010 so as to configure the processing arrangement to execute certain exemplary procedures, processes and methods, as described herein above, for example.

Further, the exemplary processing arrangement 2010 can be provided with or include an input/output arrangement 2070, which can include, e.g., a wired network, a wireless network, the internet, an intranet, a data collection probe, a sensor, etc. As shown, the exemplary processing arrangement 2010 can be in communication with an exemplary display arrangement 2060, which, according to certain exemplary embodiments of the present disclosure, can be a touch-screen configured for inputting information to the processing arrangement in addition to outputting information from the processing arrangement, for example. Further, the exemplary display 2060 and/or a storage arrangement 2050 can be used to display and/or store data in a user-accessible format and/or user-readable format.

Figure 21:
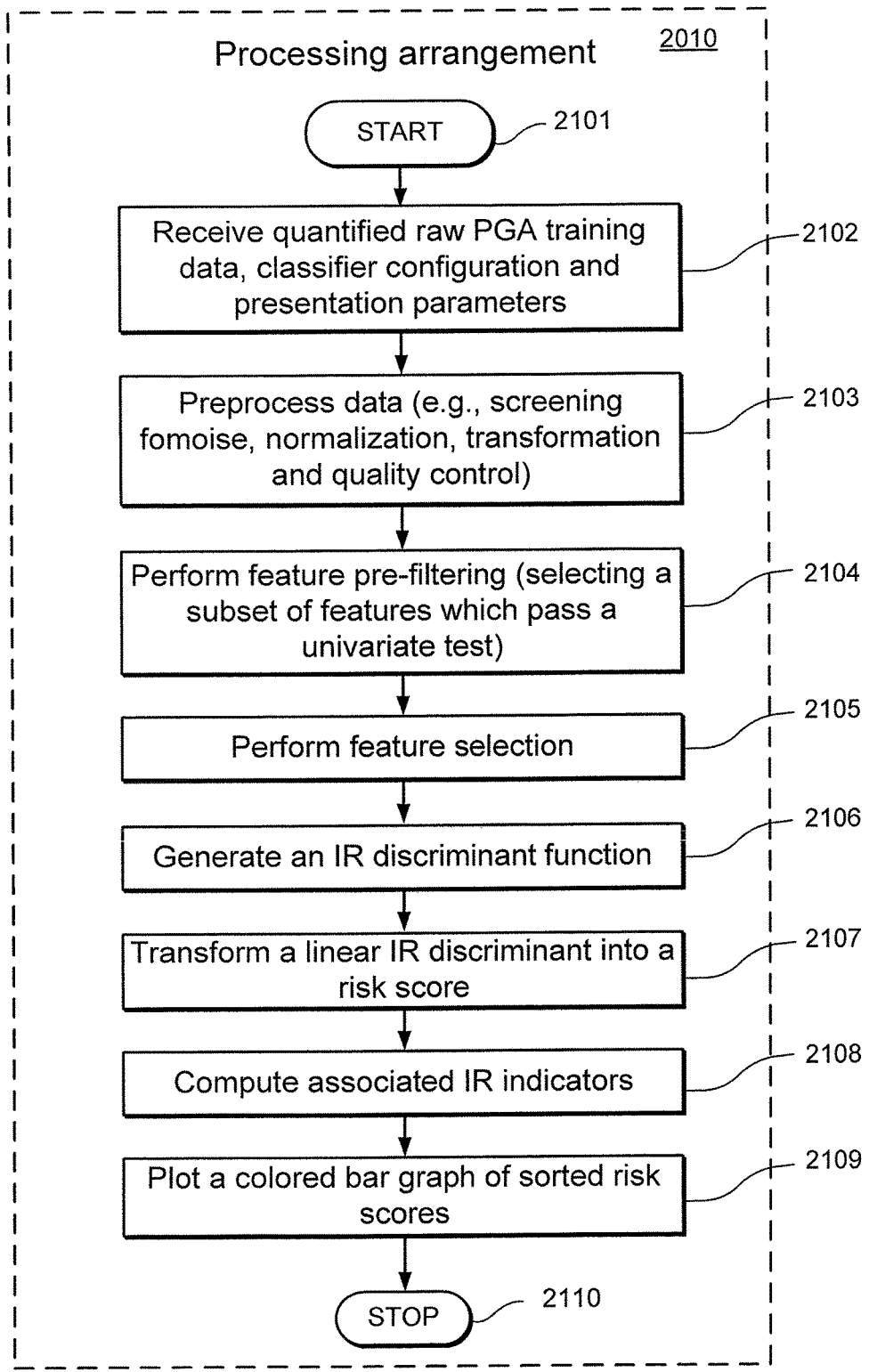
FIG. 21 is a block/flow diagram of an exemplary IR method in accordance with certain exemplary embodiments of the present disclosure.

FIG. 21 shows an illustration of a flow diagram of a procedure in accordance with certain exemplary embodiments of the present disclosure. As shown in FIG. 21, the exemplary procedure can be executed on and/or by, e.g., the processing arrangement 2010. For example, starting at subprocess 2101, the exemplary procedure can, in subprocess 2102, receive quantified raw PGA training data, classifier configuration and presentation parameters. In subprocess 2130, the exemplary procedure can reprocess data (e.g., screening for noise, normalization, transformation and quality control). Then, in subprocess 2104, the exemplary procedure can perform feature pre-filtering (e.g., selecting a subset of features which pass a univariate test). The exemplary procedure can then, in subprocess 2105, perform a feature selection procedure. Then, in subprocess 2106, the exemplary procedure can generate an IR discriminant function, and in subprocess 2107, transform a linear IR discriminant into a risk score. In subprocess 2108, the exemplary procedure can compute associated IR indicators before plot a colored bar graph of sorted risk scores in subprocess 2109.

Examples in this document are used solely to explain and illustrate the basic concepts of IR, not to demonstrate the strength of existing data and platform, for example. The examples described herein can be based on, e.g., exemplary mesothelioma assay with 65 asbestos exposed subjects (control sample) and 50 patients diagnosed with malignant mesothelioma (case sample). The data can be obtained, e.g., on the original platform and with original glycan library (e.g., with 211 glycans termed "PGA version 6"). The exemplary choice of selected feature size was thus chosen for the exemplary embodiments described herein to provide an exemplary cross-validation tests, instead of selecting larger glycan sets which could give larger training precisions, and can be, e.g., subject of overfitting.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and methods which, although not explicitly shown or described herein, embody the principles of the disclosure and are thus within the spirit and scope of the disclosure. In addition, all publications and references referred to above are incorporated herein by reference in their entireties. It should be understood that the exemplary procedures described herein can be stored on any computer accessible medium, including a hard drive, RAM, ROM, removable disks, CD-ROM, memory sticks, etc., and executed by a processing arrangement which can be a microprocessor, mini, macro, mainframe, etc. In addition, to the extent that the prior art knowledge has not been explicitly incorporated by reference herein above, it is explicitly incorporated herein in its entirety. All publications referenced above are incorporated herein by reference in their entireties.

What is claimed is:

1. A non-transitory computer-accessible medium having instructions thereon for determining probabilistic cancer information about at least one patient, wherein, when a computing arrangement executes the instructions, the computing arrangement is configured to execute procedures comprising:
 (a) receiving serum information related to a serum received from the at least one patient;
 (b) receiving Printed Glycan Array (PGA) information including a set of glycans determined using a training procedure applied to further serum information, wherein the further serum information is related to further serums received from a plurality of further patients;
 (c) generating further PGA information from the serum information by selecting a further set of glycans based on the set of glycans; and
 (d) determining the probabilistic cancer information by applying the further PGA information to the PGA information.

2. The computer-accessible medium of claim 1, wherein the scalar quantities comprise continuous scalar quantities.

3. The computer-accessible medium of claim 1, wherein the computing arrangement is configured to determine the probabilistic cancer information by:
 assigning, to each of a plurality of objects associated with the further PGA information, a scalar quantity that has a respective value;
 providing the scalar quantity assigned to each of the objects in a single diagram; and
 sorting the scalar quantities by respective magnitudes, and grouping the scalar quantities according to the respective values thereof.

4. The computer-accessible medium of claim 3, wherein the scalar quantities are grouped according to the respective values.

5. The computer-accessible medium of claim 3, wherein at least one of the scalar quantities is provided as a bar in a bar graph.

6. The computer-accessible medium of claim 5, wherein the providing procedure includes assigning each bar with a particular color based the respective value of the corresponding scalar quantities.

7. The computer-accessible medium of claim 6, wherein each of the colors corresponds to one of the groups formed by the grouping procedure.

8. The computer-accessible medium of claim 7, wherein each of the bars representing a respective value within lower or upper quartiles of each of the groups is assigned a particular shade of the color corresponding to the group.

9. The computer-accessible medium of claim 5, wherein the bar graph includes a cutoff line determined as a function of the respective values.

10. The computer-accessible medium of claim 9, wherein the computing arrangement is further configured to determine the cutoff line using at least one of a specificity or a sensitivity of the objects.

11. The computer-accessible medium of claim 5, wherein the computing arrangement is further configured to classify at least one of the scalar quantities, and assigns a bar representing a value associated with the classified scalar quantity with a color that is different than a color associated with any of the groups generated by the grouping procedure.

12. The computer-accessible medium of claim 3, wherein the computing arrangement is further configured to determine the value of each of the scalar quantities by a linear combination of predictor variables associated with each of the objects, wherein the predictor variables are continuous quantities which characterize at least one inherent property of each of the groups of the objects.

13. The computer-accessible medium of claim 12, wherein the at least one inherent property includes at least one of (i) a binding characteristic of a type of antibodies from a human serum to a library of carbohydrates on a printed glycan array, or (ii) a gene expression on a nucleic acid array.

14. The computer-accessible medium of claim 12, wherein the training procedure is based on predictor variables, which are based on historical information associated with at least one of the objects so as to train the computing arrangement.

15. The computer-accessible medium of claim 3, wherein the computing arrangement is further configured to determine the linear combination using a set of coefficients obtained by at least one of (i) a logistic regression procedure, (ii) a linear regression procedure, (iii) a linear discriminant analysis procedure, or (iv) a support vector machine.

16. The computer-accessible medium of claim 3, wherein the computing arrangement is further configured to adjust each of the values to make the respective values negative for most of the objects of a first group of the groups, and to make the respective values positive for most of objects of a second group of the groups.

17. The computer-accessible medium of claim 16, wherein the values for most of the objects of the first group are less than 0.5, and the respective values for most of the objects of the second group are greater than 0.5.

18. The computer-accessible medium of claim 3, wherein the computing arrangement is further configured to normalize each of the values to be between zero and one.

19. The computer-accessible medium of claim 3, wherein the computing arrangement is further configured to determine the respective value of each of the scalar quantities as a natural logarithm of a ratio of a first distance between the respective value of one of the objects to a center of mass of one group obtained by the grouping procedure, and second distance between the value of the one of the objects to a center of mass of another group obtained by the grouping procedure, wherein the distance is determined based on at least one of a Mahalanobis distance or a Hotelling distance.

20. The computer-accessible medium of claim 3, wherein the scalar quantities are sorted in an increasing numerical order of the respective values from a smallest value to a largest value.

21. The computer-accessible medium of claim 1, wherein the probabilistic cancer information includes at least one of (i) a probability that the at least one patient has an elevated cancer risk, (ii) a probability of a malignancy progression recurrence for the at least one patient, or (iii) a probability of survival from cancer by the at least one patient.

22. A method for determining probabilistic cancer information about at least one patient, comprising:
 (a) receiving serum information related to a serum received from the at least one patient;
 (b) receiving Printed Glycan Array (PGA) information including a set of glycans determined using a training procedure applied to further serum information, wherein the further serum information is related to further serums received from a plurality of further patients;
 (c) generating further PGA information from the serum information by selecting a further set of glycans based on the set of glycans; and
 (d) using a computer arrangement, determining the probabilistic cancer information by applying the further PGA information to the PGA information.

23. The method of claim 22, further comprising at least one of displaying or storing information associated with at least one of (i) sorting of scalar quantities associated with the serum, or (ii) grouping of the scalar quantities associated with the serum, in a storage arrangement in at least one of a user-accessible format or a user-readable format.

24. The method of claim 22, wherein the probabilistic cancer information includes at least one of (i) a probability that the at least one patient has an elevated cancer risk, (ii) a probability of a malignancy progression recurrence for the at least one patient, or (iii) a probability of survival from cancer by the at least one patient.

25. A system for determining probabilistic cancer information about at least one patient, comprising:
 a non-transitory computer-accessible medium having executable instructions thereon, wherein when at least one computing arrangement executes the instructions, the at least one computing arrangement is configured to:
 (a) receive serum information related to a serum received from the at least one patient;
 (b) receive Printed Glycan Array (PGA) information including a set of glycans determined using a training procedure applied to further serum information, wherein the further serum information is related to further serums received from a plurality of further patients;
 (c) generate further PGA information from the serum information by selecting a further set of glycans based on the set of glycans; and
 (d) determine the probabilistic cancer information by applying the further PGA information to the PGA information.

26. The system of claim 25, wherein the probabilistic cancer information includes at least one of (i) a probability that the at least one patient has an elevated cancer risk, (ii) a probability of a malignancy progression recurrence for the at least one patient, or (iii) a probability of survival from cancer by the at least one patient.

* * * * *